(12) United States Patent
Blomquist et al.

(10) Patent No.: US 8,414,523 B2
(45) Date of Patent: Apr. 9, 2013

(54) INFUSION PUMP WITH ADD-ON MODULES

(75) Inventors: Michael Blomquist, Blaine, MN (US); Timothy Bresina, Shoreview, MN (US); William Van Dyke, Inver Grove Heights, MN (US); Gail Beth Bynum, Brooklyn Park, MN (US); Michael Welsch, Stillwater, MN (US)

(73) Assignee: Tandem Diabetes Care, Inc., San Diego, CA (US)

( * ) Notice: Subject to any disclaimer, the term of this patent is extended or adjusted under 35 U.S.C. 154(b) by 0 days.

(21) Appl. No.: 12/914,295

(22) Filed: Oct. 28, 2010

(65) Prior Publication Data

US 2011/0040251 A1    Feb. 17, 2011

Related U.S. Application Data

(62) Division of application No. 11/971,351, filed on Jan. 9, 2008, now abandoned.

(51) Int. Cl.
*A61M 31/00* (2006.01)
(52) U.S. Cl. ............................................ 604/67; 604/65
(58) Field of Classification Search .............. 604/65–67, 604/118–121, 131–155, 890.1, 892.1; 417/475
See application file for complete search history.

(56) References Cited

U.S. PATENT DOCUMENTS

| | | | |
|---|---|---|---|
| 4,393,365 A | 7/1983 | Kondo | |
| 4,475,901 A | 10/1984 | Kraegen et al. | |
| 5,122,362 A | 6/1992 | Phillips et al. | |
| 5,181,910 A | 1/1993 | Scanlon | |
| 5,311,175 A | 5/1994 | Waldman | |
| 5,338,157 A | 8/1994 | Blomquist | |
| 5,364,346 A | 11/1994 | Schrezenmeir | |
| 5,368,562 A | 11/1994 | Blomquist et al. | |
| 5,389,078 A | 2/1995 | Zalesky et al. | |
| 5,485,408 A | 1/1996 | Blomquist | |
| 5,569,186 A | 10/1996 | Lord et al. | |
| 5,658,250 A | 8/1997 | Blomquist et al. | |
| 5,658,252 A | 8/1997 | Johnson | |

(Continued)

FOREIGN PATENT DOCUMENTS

| | | |
|---|---|---|
| DE | 4407005 | 3/1995 |
| DE | 10121317 | 11/2002 |

(Continued)

OTHER PUBLICATIONS

Plougmann et al, "DiasNet—a diavetes advisory system for communication and education via the internet", International Journal of Medical Informatics, vol. 26. pp. 319-330 (2001).

(Continued)

*Primary Examiner* — Nicholas Lucchesi
*Assistant Examiner* — Gerald Landry, II
(74) *Attorney, Agent, or Firm* — Patterson Thuente Pedersen, P.A.

(57) ABSTRACT

This document discusses, among other things, an apparatus comprising a pump configured to deliver a fluid, a wireless communication port, a controller, and a housing to enclose the apparatus. The controller is configured to communicate with a second device via the communication port using an open standard wireless communication protocol. The housing includes a mechanical coupling to slidably engage the second device which includes a second wireless communication port. Slidably engaging the second device positions the first and second communication ports opposite each other to allow communication via the first and second communication ports when slidably engaged.

18 Claims, 14 Drawing Sheets

U.S. PATENT DOCUMENTS

| | | | |
|---|---|---|---|
| 5,665,065 A | 9/1997 | Colman et al. | |
| 5,669,877 A | 9/1997 | Blomquist | |
| 5,685,844 A | 11/1997 | Marttila | |
| 5,695,473 A | 12/1997 | Olsen | |
| 5,713,856 A | 2/1998 | Eggers et al. | |
| 5,810,771 A | 9/1998 | Blomquist | |
| 5,814,015 A | 9/1998 | Gargano et al. | |
| 5,822,715 A | 10/1998 | Worthington et al. | |
| 5,876,370 A | 3/1999 | Blomquist | |
| 5,879,143 A | 3/1999 | Cote et al. | |
| 5,935,099 A | 8/1999 | Peterson et al. | |
| 5,935,106 A | 8/1999 | Olsen | |
| 6,024,539 A | 2/2000 | Blomquist | |
| 6,077,055 A | 6/2000 | Vilks | |
| 6,241,704 B1 | 6/2001 | Peterson et al. | |
| 6,248,057 B1 | 6/2001 | Mavity et al. | |
| 6,248,067 B1 | 6/2001 | Causey, III et al. | |
| 6,422,057 B1 | 7/2002 | Anderson | |
| 6,475,180 B2 | 11/2002 | Peterson et al. | |
| 6,544,212 B2 | 4/2003 | Galley et al. | |
| 6,551,276 B1 | 4/2003 | Mann et al. | |
| 6,554,798 B1 | 4/2003 | Mann et al. | |
| 6,558,320 B1 | 5/2003 | Causey, III et al. | |
| 6,558,351 B1 | 5/2003 | Steil et al. | |
| 6,562,001 B2 | 5/2003 | Lebel et al. | |
| 6,577,899 B2 | 6/2003 | Lebel et al. | |
| 6,641,533 B2 | 11/2003 | Causey, III et al. | |
| 6,744,350 B2 | 6/2004 | Blomquist | |
| 6,790,198 B1 | 9/2004 | White et al. | |
| 6,809,653 B1 | 10/2004 | Mann et al. | |
| 6,852,104 B2 | 2/2005 | Blomquist | |
| 6,872,200 B2 | 3/2005 | Mann et al. | |
| 6,934,220 B1 | 8/2005 | Cruitt et al. | |
| 6,936,029 B2 | 8/2005 | Mann et al. | |
| 6,979,326 B2 | 12/2005 | Mann et al. | |
| 6,997,920 B2 | 2/2006 | Mann et al. | |
| 7,025,743 B2 | 4/2006 | Mann et al. | |
| 7,033,338 B2 | 4/2006 | Vilks et al. | |
| 7,041,082 B2 | 5/2006 | Blomquist et al. | |
| 7,098,803 B2 | 8/2006 | Mann et al. | |
| 7,109,878 B2 | 9/2006 | Mann et al. | |
| 7,179,226 B2 | 2/2007 | Crothall et al. | |
| 7,267,665 B2 | 9/2007 | Steil et al. | |
| 7,278,983 B2 | 10/2007 | Ireland et al. | |
| 7,291,107 B2 | 11/2007 | Hellwig et al. | |
| 7,307,245 B2 | 12/2007 | Faries, Jr. et al. | |
| 7,324,012 B2 | 1/2008 | Mann et al. | |
| 7,341,577 B2 | 3/2008 | Gill | |
| 7,399,277 B2 | 7/2008 | Saidara et al. | |
| 7,515,060 B2 | 4/2009 | Blomquist | |
| 7,559,926 B1 | 7/2009 | Blischak | |
| 7,715,893 B2 | 5/2010 | Kamath et al. | |
| 7,734,323 B2 | 6/2010 | Blomquist et al. | |
| 7,751,907 B2 | 7/2010 | Blomquist | |
| 2001/0031944 A1 | 10/2001 | Peterson et al. | |
| 2001/0037217 A1 | 11/2001 | Abensour et al. | |
| 2002/0002326 A1 | 1/2002 | Causey, III et al. | |
| 2002/0065454 A1 | 5/2002 | Lebel et al. | |
| 2002/0072932 A1 | 6/2002 | Swamy | |
| 2002/0107476 A1 | 8/2002 | Mann et al. | |
| 2002/0183693 A1 | 12/2002 | Peterson et al. | |
| 2002/0193679 A1 | 12/2002 | Malave et al. | |
| 2003/0032867 A1 | 2/2003 | Crothall et al. | |
| 2003/0050621 A1 | 3/2003 | Lebel et al. | |
| 2003/0060765 A1 | 3/2003 | Campbell et al. | |
| 2003/0065308 A1 | 4/2003 | Lebel et al. | |
| 2003/0088238 A1* | 5/2003 | Poulsen et al. | 604/890.1 |
| 2003/0114836 A1 | 6/2003 | Estes et al. | |
| 2003/0130616 A1 | 7/2003 | Steil et al. | |
| 2003/0163088 A1 | 8/2003 | Blomquist | |
| 2003/0163090 A1 | 8/2003 | Blomquist et al. | |
| 2003/0208113 A1 | 11/2003 | Mault et al. | |
| 2003/0212364 A1 | 11/2003 | Mann et al. | |
| 2003/0236489 A1* | 12/2003 | Jacobson et al. | 604/67 |
| 2004/0015102 A1 | 1/2004 | Cummings et al. | |
| 2004/0068230 A1 | 4/2004 | Estes et al. | |
| 2004/0073095 A1 | 4/2004 | Causey, III et al. | |
| 2004/0115067 A1 | 6/2004 | Rush et al. | |
| 2004/0180810 A1 | 9/2004 | Pilarski | |
| 2004/0254434 A1 | 12/2004 | Goodnow et al. | |
| 2005/0021006 A1 | 1/2005 | Tonnies | |
| 2005/0022274 A1 | 1/2005 | Campbell et al. | |
| 2005/0030164 A1 | 2/2005 | Blomquist | |
| 2005/0050621 A1 | 3/2005 | Thomas | |
| 2005/0065760 A1 | 3/2005 | Murtfeldt et al. | |
| 2005/0095063 A1* | 5/2005 | Fathallah et al. | 403/381 |
| 2005/0137530 A1 | 6/2005 | Campbell et al. | |
| 2005/0143864 A1 | 6/2005 | Blomquist | |
| 2005/0171513 A1 | 8/2005 | Mann et al. | |
| 2005/0197553 A1 | 9/2005 | Cooper | |
| 2005/0197621 A1 | 9/2005 | Poulsen et al. | |
| 2005/0277872 A1 | 12/2005 | Colby et al. | |
| 2006/0001550 A1 | 1/2006 | Mann et al. | |
| 2006/0014670 A1 | 1/2006 | Green et al. | |
| 2006/0047192 A1 | 3/2006 | Hellwig et al. | |
| 2006/0047538 A1 | 3/2006 | Condurso et al. | |
| 2006/0080059 A1 | 4/2006 | Stupp et al. | |
| 2006/0122577 A1 | 6/2006 | Poulsen et al. | |
| 2006/0132292 A1 | 6/2006 | Blomquist | |
| 2006/0137695 A1 | 6/2006 | Hellwig et al. | |
| 2006/0173406 A1 | 8/2006 | Hayes et al. | |
| 2006/0173444 A1 | 8/2006 | Choy et al. | |
| 2006/0202859 A1 | 9/2006 | Mastrototaro et al. | |
| 2006/0253097 A1 | 11/2006 | Braig et al. | |
| 2006/0264895 A1 | 11/2006 | Flanders | |
| 2006/0276771 A1 | 12/2006 | Galley et al. | |
| 2007/0016127 A1 | 1/2007 | Staib et al. | |
| 2007/0021733 A1* | 1/2007 | Hansen et al. | 604/890.1 |
| 2007/0060796 A1 | 3/2007 | Kim | |
| 2007/0060871 A1 | 3/2007 | Istoc et al. | |
| 2007/0100222 A1 | 5/2007 | Mastrototaro et al. | |
| 2007/0112299 A1* | 5/2007 | Smit et al. | 604/67 |
| 2007/0124002 A1 | 5/2007 | Estes et al. | |
| 2007/0156033 A1 | 7/2007 | Causey, III et al. | |
| 2007/0203454 A1* | 8/2007 | Shermer et al. | 604/135 |
| 2007/0233051 A1 | 10/2007 | Hohl et al. | |
| 2007/0255250 A1 | 11/2007 | Moberg et al. | |
| 2008/0004601 A1 | 1/2008 | Jennewine et al. | |
| 2008/0030369 A1 | 2/2008 | Mann et al. | |
| 2008/0033357 A1 | 2/2008 | Mann et al. | |
| 2008/0051709 A1* | 2/2008 | Mounce et al. | 604/131 |
| 2008/0051714 A1* | 2/2008 | Moberg et al. | 604/135 |
| 2008/0071251 A1 | 3/2008 | Moubayed et al. | |
| 2008/0097289 A1 | 4/2008 | Steil et al. | |
| 2008/0106431 A1 | 5/2008 | Blomquist | |
| 2008/0147050 A1 | 6/2008 | Mann et al. | |
| 2008/0172026 A1 | 7/2008 | Blomquist | |
| 2008/0172027 A1 | 7/2008 | Blomquist | |
| 2008/0172028 A1 | 7/2008 | Blomquist | |
| 2008/0172029 A1 | 7/2008 | Blomquist | |
| 2008/0172030 A1 | 7/2008 | Blomquist | |
| 2008/0172031 A1 | 7/2008 | Blomquist | |
| 2008/0177165 A1 | 7/2008 | Blomquist et al. | |
| 2008/0206799 A1 | 8/2008 | Blomquist | |
| 2008/0228056 A1 | 9/2008 | Blomquist et al. | |
| 2008/0269585 A1 | 10/2008 | Ginsberg | |
| 2008/0287922 A1 | 11/2008 | Panduro | |
| 2008/0294294 A1 | 11/2008 | Blomquist | |
| 2008/0300534 A1 | 12/2008 | Blomquist | |
| 2009/0088731 A1 | 4/2009 | Campbell et al. | |
| 2009/0105646 A1* | 4/2009 | Hendrixson et al. | 604/135 |
| 2009/0131860 A1* | 5/2009 | Nielsen | 604/66 |
| 2009/0177142 A1 | 7/2009 | Blomquist et al. | |
| 2009/0177147 A1 | 7/2009 | Blomquist et al. | |
| 2009/0177154 A1 | 7/2009 | Blomquist | |
| 2010/0056993 A1 | 3/2010 | Chase | |
| 2010/0057043 A1 | 3/2010 | Kovatchev et al. | |
| 2010/0222765 A1 | 9/2010 | Blomquist et al. | |
| 2010/0274751 A1 | 10/2010 | Blomquist | |
| 2011/0033833 A1 | 2/2011 | Blomquist et al. | |

FOREIGN PATENT DOCUMENTS

| | | |
|---|---|---|
| DE | 10352456 | 7/2005 |
| EP | 1102194 | 5/2001 |
| EP | 1571582 | 9/2005 |
| WO | WO 00/45696 | 8/2000 |
| WO | WO0074753 | 12/2000 |

| | | |
|---|---|---|
| WO | WO01/52727 | 7/2001 |
| WO | WO02062212 | 8/2002 |
| WO | WO2005046559 | 5/2005 |
| WO | WO2006/061169 | 6/2006 |
| WO | WO2007056592 | 5/2007 |
| WO | WO2007089537 | 8/2007 |
| WO | WO2007/149533 | 12/2007 |
| WO | WO2008/048582 | 4/2008 |
| WO | WO2008048556 | 4/2008 |
| WO | WO2008048583 | 4/2008 |
| WO | WO2008048584 | 4/2008 |
| WO | WO2008048585 | 4/2008 |
| WO | WO2008048586 | 4/2008 |
| WO | WO2008048587 | 4/2008 |
| WO | WO2008091320 | 7/2008 |
| WO | WO2008/112078 | 9/2008 |
| WO | WO2008153689 | 12/2008 |
| WO | WO2008153819 | 12/2008 |
| WO | WO2009088983 | 7/2009 |
| WO | WO2009089028 | 7/2009 |
| WO | WO2009089029 | 7/2009 |

OTHER PUBLICATIONS

Wilinska et al., "Insulin Kinetics in Type-1 Diabetes: Continuous and Bolus Delivery of Reapid Acting Insulin>" IEEE Transactions on Bopmedical Engineering vol. 52. No. 1, pp. 3-12. Jan. 2005.
Bott et al, "Impact of Smoking on the Metabolic Action of Subcutaneous Regular Insulin in Type 2 Diabetic Patients" Horm. Metab. Res., vol. 37, pp. 445-449 (2005).
Puckett eta l., Am. J. Physiol. vol. 269, p. E1115-E1124, 1995.
Wach et al., Med & Biol. Eng & comput., vol. 33, p. 18-23, 1995.
Lehman et al., Artifical Intelligence in Medicine, vol. 6, p. 137-160,1994.
"The Use of Insulin Pumps With Meal Bolus Alarms in Children With Type 1 Diabetes to Improve Glycemic Control", Diabetes Carem vol. 29, No. 5. May 2006. 1012-1015.
Compare Insulin Pump for Diabetes, 4 pages. Printed from www.diabetesnet.com/diabetes_technology/insulin_pump_models.php. Jun. 18, 2009.
Deltec Cozmo. Personalized Insulin Pump. Starting Guide. Internet Article. Smiths Medical., 2004. pp. 1-83. XP002497833.
European Office Action from European Application No. 08779626.4 mailed May 25, 2010.
European Office Action from European Application No. 08767734.6 dated Apr. 7, 2010.
International Search Report for International Application No. PCT/US2007/022050 mailed Mar. 7, 2008.
International Search Report for International Application No. PCT/US09/00107 dated May 4, 2009.
International Search Report for International Application No. PCT/US2008/002536 dated Sep. 4, 2008.
International Search Report for International Application No. PCT/US07/024424 dated Mar. 6, 2009.
International Search Report for International Application No. PCT/US2008/006449 mailed Oct. 10, 2008.
International Search Report for International Application No. PCT/US2008/006801 mailed Oct. 30, 2008.
International Search Report for International Application No. PCT/US2009/000034 dated May 27, 2009.
International Search Report for International Application No. PCT/US2009/000106 dated May 13, 2009.
International Search Report from International Application No. PCT/US2007/024423 dated May 19, 2008.
Stapel, Elizabeth, "Converting Between Decimals, Fractions, and Percents", Purplemath. 2006. http://www.purplemath.com/modules/percents2.htm.
Walsh et al., "Diabetes Technology—Concept 1: Super Bolus" (online) http://www.diabetesnet.com/diabetes_technology/super_bolus.php>. Sep. 17, 2007. 3 pages.
Walsh et al., "Pumping Insulin: Everything You Need for Success on a Smart Insulin Pump", Torrey Pines Press. San Diego. ISBN 1-884804-86-1, 2006.
Walsh et al., "Select & Test Your Basal Rates", Pumping Insulin, Fourth Edition, Chapter 11 (2006). 30 pages.
Walsh et al., "Select and Test Your Carb Factor", Pumping Insulin, Fourth Edition, Chapter 12. (2006). 32 pages.
Wikipedia's definition for "basal rate", 1 page. Printed from wikipedia.com.
Written Opinion for International Application No. PCT/US09/00107 dated May 4, 2009.
Written Opinion for International Application No. PCT/US2007/022050 mailed Mar. 7, 2008.
Written Opinion for International Application No. PCT/US2008/002536 dated Sep. 4, 2008.
Written Opinion for International Application No. PCT/US2008/006449 dated Oct. 10, 2008.
Written Opinion for International Application No. PCT/US2008/006801 mailed Oct. 30, 2008.
Written Opinion for International Application No. PCT/US2009/000034 dated May 27, 2009.
Written Opinion for International Application No. PCT/US2009/000106 dated May 13, 2009.
Written Opinion from International Application No. PCT/US2007/024423 dated May 19, 2008.
International Search Report for International Application No. PCT/US2007/022046 dated Mar. 7, 2008.
Written Opinion for International Application No. PCT/US2007/022046 dated Mar. 7, 2008.
Trajanoski et al., Pharmacokinetic Model for the Absorption of Subcutaneoutsly Injected Soluble Insulin and Monomeric Insulin Analogues. Biomedizinische Technik,. vol. 38 No. 9. Sep. 1, 1993.
Hildebrandt, Subcutaneous Absorption of Insulin in Insulin-Dependent Diavetic patients. Influence of Species Physico-Chemcial properties of Insulin and Physiological factors. Danish Medical Bulletin. Aug. 1991.
Written Opinion for International Application No. PCT/US2007/022004 dated Oct. 9, 2008.
Walsh et al., "Select & Test Your Correction Factor", Pumping Insulin, Fourth Edition, Chapter 13. (2006).
Written Opinion for International Application No. PCT/US2007/024424 mailed Mar. 6, 2009.
International Search Report for International Application No. PCT/US2007/022004 dated Oct. 9, 2008.
Written Opinion for International Application No. PCT/US2007/022047 dated Mar. 7, 2008.
International Search Report for International Application No. PCT/US2007/022047 dated Mar. 7, 2008.
Written Opinion for International Application No. PCT/US2007/022048 dated Mar. 7, 2008.
International Search Report for International Application No. PCT/US2007/022048 dated Mar. 7, 2008.
Written Opinion for International Application No. PCT/US2007/022049 dated Mar. 7, 2008.
International Search Report for International Application No. PCT/US2007/022049 dated Mar. 7, 2008.
International Search Report for International Application No. PCT/US2007/022051 dated Mar. 7, 2008.
Written Opinion for International Application No. PCT/US2007/022051 mailed Mar. 7, 2008.
International Search Report for International Application No. PCT/US2007/002052 dated May 11, 2007.
Written Opinion for International Application No. PCT/US2007/022052 mailed May 11, 2007.
European Office Action from European Application No. 07852760.3 dated Aug. 11, 2010.
Application and File History for U.S. Appl. No. 12/720,306, filed Mar. 9, 2010, inventor Blomquist et al.
Application and File History for U.S. Appl. No. 11/582,841, filed Oct. 17, 2006, inventor Blomquist.
Application and File History for U.S. Appl. No. 11/626,653, filed Jan. 24, 2007, inventors Blomquist et al.
Application and File History for U.S. Appl. No. 11/753,420, filed May 24, 2007, inventor Blomquist.
Application and File History for U.S. Appl. No. 11/018,706, filed Dec. 20, 2004, inventor Blomquist.
Application and File History for U.S. Appl. No. 11/582,519, filed Oct. 17, 2006, inventor Blomquist.

Application and File History for U.S. Appl. No. 11/582,823, filed Oct. 17, 2006, inventor Blomquist.
Application and File History for U.S. Appl. No. 11/970,232, filed Jan. 7, 2008, inventor Blomquist.
Application and File History for U.S. Appl. No. 11/679,712, filed Feb. 27, 2007 inventor Blomquist.
Application and File History for U.S. Appl. No. 11/685,617, filed Mar. 13, 2007 inventor Blomquist et al.
Application and File History for U.S. Appl. No. 11/755,480, filed May 30, 2007, inventor Blomquist.
Application and File History for U.S. Appl. No. 11/971,351, filed Jan. 9, 2008 inventor Blomquist.
Application and File History for U.S. Appl. No. 12/774,991, filed May 6, 2010 inventor Blomquist.
Application and File History for U.S. Appl. No. 11/970,691, filed Jan. 8, 2008, inventor Blomquist.
Application and File History for U.S. Appl. No. 11/582,831, filed Oct. 17, 2006, inventor Blomquist.
Application and File History for U.S. Appl. No. 11/582,845, filed Oct. 17, 2006, inventor Blomquist.
Application and File History for U.S. Appl. No. 11/582,877, filed Oct. 17, 2006, inventor Blomquist.
Application and File History for U.S. Appl. No. 11/582,879, filed Oct. 17, 2006, inventor Blomquist.
U.S. Appl. No. 11/582,841, filed Oct. 17, 2006, inventor Blomquist.
U.S. Appl. No. 11/626,653, filed Jan. 24, 2007, inventors Blomquist et al.
U.S. Appl. No. 11/753,420, filed May 24, 2007, inventor Blomquist.
U.S. Appl. No. 12/720,306, filed Mar. 9, 2010 inventors Blomquist et al.
U.S. Appl. No. 11/018,706, filed Dec. 20, 2004, inventor Blomquist.
U.S. Appl. No. 11/582,519, filed Oct. 17, 2006, inventor Blomquist.
U.S. Appl. No. 11/582,823, filed Oct. 17, 2006, inventor Blomquist.
U.S. Appl. No. 11/970,232, filed Jan. 7, 2008, inventor Blomquist.
U.S. Appl. No. 11/679,712, filed Feb. 27, 2007 inventor Blomquist.
U.S. Appl. No. 11/685,617, filed Mar. 13, 2007 inventor Blomquist et al.
U.S. Appl. No. 11/755,480, filed May 30, 2007, inventor Blomquist.
U.S. Appl. No. 11/971,351, filed Jan. 9, 2008 inventor Blomquist.
U.S. Appl. No. 12/774,991, filed May 6, 2010 inventor Blomquist.
U.S. Appl. No. 11/970,691, filed Jan. 8, 2008, inventor Blomquist.
U.S. Appl. No. 12/908,218, filed Oct. 20, 2010 inventor Blomquist.
U.S. Appl. No. 11/582,831, filed Oct. 17, 2006, inventor Blomquist.
U.S. Appl. No. 11/582,845, filed Oct. 17, 2006, inventor Blomquist.
U.S. Appl. No. 11/582,877, filed Oct. 17, 2006, inventor Blomquist.
U.S. Appl. No. 11/582,879, filed Oct. 17, 2006, inventor Blomquist.

* cited by examiner

INFUSION PUMP WITH ADD-ON MODULES

RELATED APPLICATION

This application is a divisional of application Ser. No. 11/971,351 filed Jan. 9, 2008, which is hereby fully incorporated herein by reference.

BACKGROUND

People who suffer from diabetes require insulin to keep their blood glucose level as close as possible to normal levels. It is essential for people with diabetes to manage their blood glucose level to within a normal range. Complications from diabetes can include heart disease (cardiovascular disease), blindness (retinopathy), nerve damage (neuropathy), and kidney damage (nephropathy). Insulin is a hormone that reduces the level of blood glucose in the body. Normally, insulin is produced by beta cells in the pancreas. In non-diabetic people, the beta cells release insulin to satisfy two types of insulin needs. The first type is a low-level of background insulin that is released throughout the day. The second type is a quick release of a higher-level of insulin in response to eating. Insulin therapy replaces or supplements insulin produced by the pancreas.

Conventional insulin therapy typically involves one or two injections a day. The low number of injections has the disadvantage of allowing larger variations in a person's insulin levels. Some people with diabetes manage their blood glucose level with multiple daily injections (MDI). MDI may involve more than three injections a day and four or more blood glucose tests a day. MDI offers better control than conventional therapy. However, insulin injections are inconvenient and require a diabetic person to track the insulin doses, the amount of carbohydrates eaten, and their blood glucose levels among other information critical to control.

It is important for a diabetic person to be treated with the proper amount of insulin. As discussed previously, high blood sugar can lead to serious complications. Conversely, a person with low blood sugar can develop hypoglycemia. Ideally, insulin therapy mimics the way the body works. An insulin pump is one way to mimic the body's insulin production. An insulin pump can provide a background or basal infusion of insulin throughout the day and provide a quick release or bolus of insulin when carbohydrates are eaten. If a person develops high blood sugar, a correction bolus can be delivered by the pump to correct it. While insulin pumps improve convenience and flexibility for a diabetic person, they can be sophisticated devices. It is desirable for an insulin pump to have features that make the pump more convenient or more effective for the patient to use.

SUMMARY

This document discusses, among other things, devices and methods for managing infusion therapy. A device example includes a pump configured to deliver a fluid, a wireless communication port, a controller, and a housing to enclose the apparatus. The controller is configured to communicate with a second device via the communication port using an open standard wireless communication protocol. The housing includes a mechanical coupling to slidably engage the second device which includes a second wireless communication port. Slidably engaging the second device positions the first and second communication ports opposite each other to allow communication via the first and second communication ports when slidably engaged.

A method example includes positioning a mechanical coupling on a housing that encloses the pump device so that the mechanical coupling slidably engages a second device, positioning a first wireless communication port in relation to the mechanical coupling such that, when the second device is in a slidably engaged position, the first wireless communication port is positioned opposite a second wireless communication port of the second device, and communicating with the second device via the first and second communication ports using an open standard wireless communication protocol.

This section is intended to provide an overview of the subject matter of the present patent application. It is not intended to provide an exclusive or exhaustive explanation of the invention. The detailed description is included to provide further information about the subject matter of the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1A:
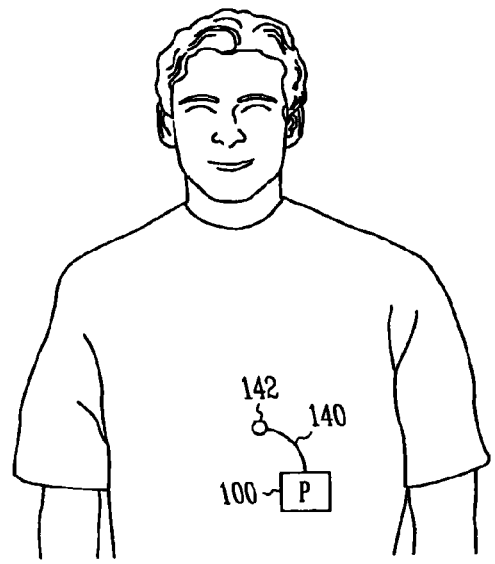
FIGS. 1A and 1B illustrate portions of a device that includes an insulin pump.
Figure 1B:
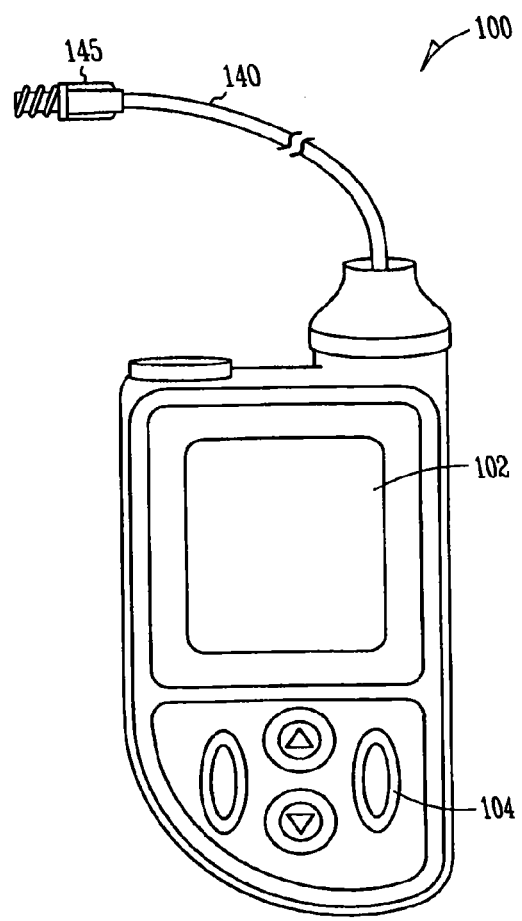

Insulin pumps can be sophisticated devices. Additional pump features may assist an insulin pump user in being more effective in treating their diabetes. FIGS. 1A and 1B illustrate portions of a device 100 that includes an insulin pump. The device 100 includes a cassette or cartridge of insulin. The cartridge is connectable to infusion tubing 140 connectable to a patient such as by a Luer lock 145 or infusion set 142. The device 100 includes a display 102 and a user interface that may include the display 102 and include one or more keys 104 in a keypad. Because it is important for an insulin pump user to properly treat their diabetes using the pump, it is desirable for a pump to have features that make the pump more convenient or more effective to use. The features may be integral to the device or may be provided by add-on modules.

Add-On Module

Figure 2:
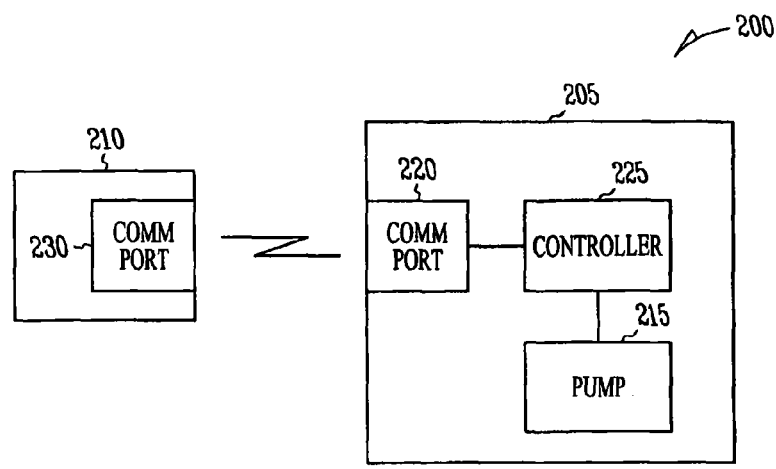
FIG. 2 is a block diagram of portions of a system to provide add-on features to an insulin pump device.

FIG. 2 is a block diagram of portions of a system 200 to provide add-on features to an insulin pump device to expand its functional capability. The system 200 includes a first device 205 and a second device 210. The first device 205 includes a pump 215 configured to deliver insulin, a first wireless communication port 220, and a controller 225.

The pump 215 may be a positive displacement pump. Descriptions of an example of a medication pump to deliver insulin are found in Vilks et al., "Cartridge and Rod for Axially Loading a Medication Pump," U.S. Pat. No. 7,033,338, filed Feb. 28, 2002, which is incorporated herein by reference in its entirety. The pump 215 may drive a plunger in a removable insulin cartridge to deliver the insulin. The first wireless communication port 220 may be an infrared (IR) communication port, or the first wireless communication port 220 may be a radio communication port (e.g., a radio frequency or RF port).

The controller 225 can be implemented using hardware circuits, firmware, software or any combination of hardware, firmware, and software. Examples, include a microcontroller, a logical state machine, a field programmable gate array (FPGA), application specific integrated circuit (ASIC), and a processor such as a microprocessor, digital signal processor, or other type of processor. The controller 225 is configured to perform or execute a function or functions. Such functions correspond to modules to provide features integral to the first device. Modules may be software, hardware, firmware or any combination thereof Multiple functions may be performed in one or more modules. In some embodiments, software or firmware is provided on a computer readable medium. The computer readable medium includes instructions therein, which when processed (such as by the controller 225 for example) results in a device performing the functions described herein. Examples of a computer readable medium include a compact disc (CD), memory stick, or remote storage accessible via a communication network such as the internet or a cell phone network.

The second device 210 includes a second wireless communication port 230. The second device 210 provides a feature or features to the first device 205 by communicating information via the wireless ports. In this way the second device 210 is an add-on module to the first device. Add-on modules perform a function or functions external to the first device 205. The functions may be performed by a controller included in the second device 210.

Figure 3:
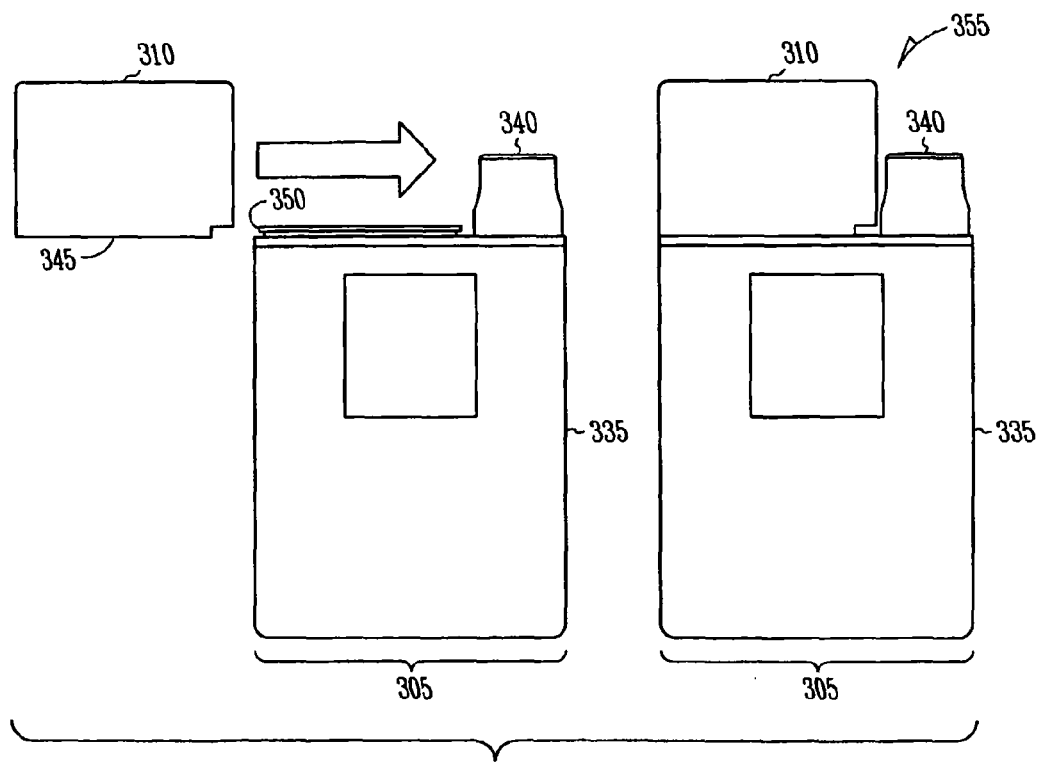
FIG. 3 is an illustration showing a mechanical coupling for an add-on module.

FIG. 3 is an illustration showing a mechanical coupling of the first device 305 and the second device 310. The first device 305 includes a housing 335 that encloses the first device 305. The housing 335 includes a mechanical coupling 350 to slidably engage the second device 310. By slidably mounting the second device 310 next to the insulin cartridge cap 340 of the first device 305, the first device 305 does not have to become any thicker and the change in effective length can be minimized by using the empty space next to the insulin cartridge cap 340. This prevents a module added-on to the insulin pump device from making the device more cumbersome for the user to wear. The slide mounting also allows for quick and easy attachment by the user; making it more likely that the user will use the add-on module.

In some embodiments, the mechanical coupling 350 includes a locking mechanism to lock the second apparatus in the slidably engaged position and the second device 310 includes a release mechanism to release the second device 310 from the slidably engaged position, or to otherwise detach the second device 310 from the first device 305. In certain embodiments, the release mechanism is a release button that may be located on a side surface 355 of the second device. In some embodiments, the second device 310 includes a battery tray that slides into the bottom surface 345 of the second device.

In some embodiments, slidably engaging the second device 310 and the first device 305 positions the first wireless communication port 220 of FIG. 2 opposite the second wireless communication port 230. This allows infrared communication ports to be aligned for communication. In some embodiments, the first device 205 and the second device 210 communicate using a proprietary protocol. In some embodiments, the first device 205 and the second device 210 communicate using an open standard wireless communication protocol. An example of an open standard wireless communication protocol includes, among other things, the Infrared Data Association (IrDA) protocol. Use of an open standard wireless communication protocol may ease development of add-on modules for the insulin pump device.

In some embodiments, the second device 210 includes a blood glucose monitor. A blood glucose monitor or meter measures blood glucose levels using a sample of blood or of interstitial fluid. Some monitors require a finger-stick to acquire the sample that is applied to a test strip to get a blood glucose reading. Some monitors are able to provide continuous monitoring of blood glucose. A continuous blood glucose monitor may include a blood glucose sensor circuit to produce an electrical blood glucose signal representative of a blood glucose level of the patient. A description of a blood glucose sensor circuit can be found in Steil et al., "Closed Loop System for Controlling Insulin Infusion," U.S. Pat. No. 6,558,351, filed Jun. 1, 2000, which is incorporated herein by reference in its entirety. The blood glucose monitor provides information regarding the blood glucose level of the user (e.g., blood glucose data) to the first device 205.

In some embodiments, the second device 210 includes a glycosylated hemoglobin ($Hb_{A1c}$) tester. When a diabetic is not effectively controlling their diabetes, blood sugar combines with hemoglobin and the hemoglobin becomes abnormally glycated. The $Hb_{A1c}$ tester determines if the $Hb_{A1c}$ level of the user is within a normal range. In some embodiments, the second device 210 includes an activity monitor. The activity monitor includes a sensor that produces an activity sensor signal that is representative of the activity of the user. In some embodiments, the activity sensor is an accelerometer. In some embodiments, the activity monitor includes a pedometer function. The activity monitor provides information related to activity of a user. In some embodiments, the second device 210 includes a blood ketone tester. Monitoring blood ketone level is useful to detect diabetic ketoacidosis. The blood ketone tester provides information regarding the blood ketone level of the user to the first device. Other embodiments of the second device 210 implement any of the features described herein.

Figure 4:
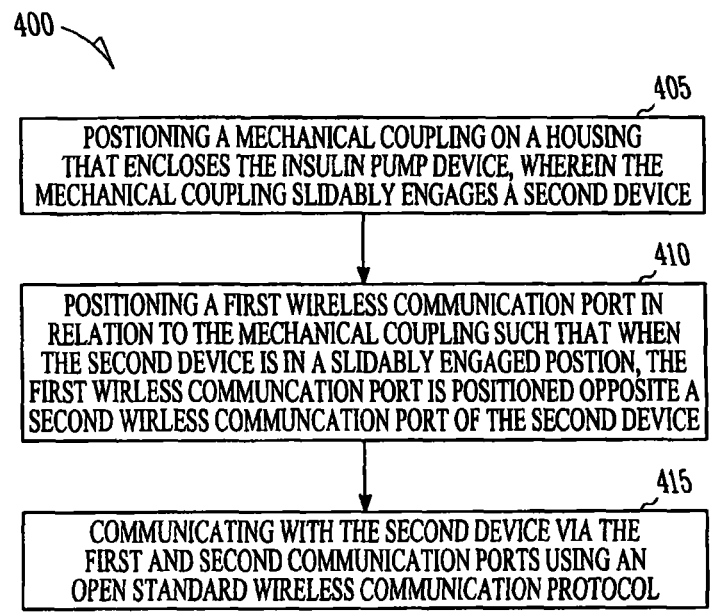
FIG. 4 shows a flow diagram of an embodiment of a method to provide add-on features to an insulin pump device.

FIG. 4 shows a flow diagram of an example of a method 400 to provide add-on features to an insulin pump device. At block 405, a mechanical coupling is positioned on a housing that encloses an insulin pump device. The mechanical coupling slidably engages a second device.

At block 410, a first wireless communication port is positioned in relation to the mechanical coupling such that when a second device is in a slidably engaged position, the first wireless communication port is positioned opposite a second wireless communication port of the second device. At block 415, the insulin pump device communicates with the second device via the first and second communication ports using an open standard wireless communication protocol.

Activity Monitoring

Activity of the insulin pump user may lead to a change in insulin therapy of the user. A pump user may not always know when activity such as exercise leads to a change in therapy, or the user may neglect to address a change required by the activity.

Figure 5:
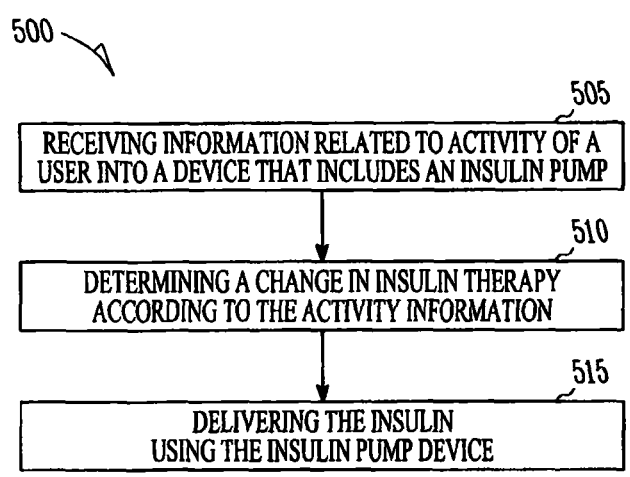
FIG. 5 shows a flow diagram of an embodiment of method to manage blood glucose of an insulin pump user in response to activity.

FIG. 5 shows a flow diagram of an embodiment of method 500 to manage blood glucose of an insulin pump user in response to activity. At block 505, information related to activity of a user is received into a device that includes an insulin pump. At block 510, a change in insulin therapy is determined according to the activity information. At block 515, the changed insulin therapy is delivered using the insulin pump device.

Figure 6:
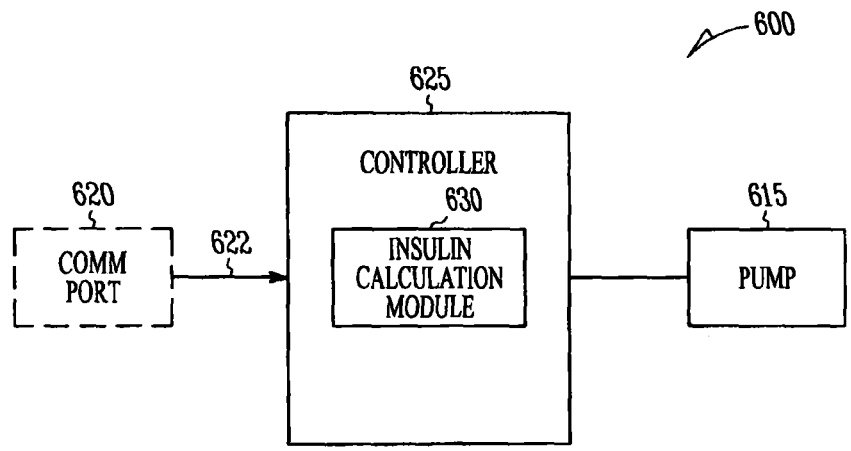
FIG. 6 is a block diagram of portions of an embodiment of a device that helps a user manage their blood glucose in response to activity.

FIG. 6 is a block diagram of portions of an embodiment of a device 600 that helps a user manage their blood glucose in response to activity. The device 600 includes a pump 615 configured to deliver insulin, an input 622, and a controller 625. The controller 625 receives information related to activity of a user of the apparatus via the input 622. In some embodiments, the device 600 includes a user interface communicatively coupled to the input 622. The communicative coupling allows the controller 6255 to exchange electrical signals with the input 622 and pump 615 even though intervening circuitry may be present. The user interface may include one or more keys in a keypad. The controller 625 receives the information related to activity of a user via the user interface.

In some embodiments, the device includes a communication port 620 and the controller 625 receives the information from a separate second device. In certain embodiments, the communication port 620 is a wired port (e.g., a universal serial bus (USB) port, Firewire port, or RS232 port). In certain embodiments, the communication port 620 is a wireless port (e.g., an IR port or an RF port).

In some embodiments, the second device that provides activity information is an add-on module that includes an activity monitor. In certain embodiments, the activity monitor attaches to the device 600 slidably as in FIG. 3. In certain embodiments, the activity monitor attaches to the device 600 by a clasp mechanism. Descriptions of devices and methods that attach add-on modules to an insulin pump device are found in Goodnow et al., "Glucose Measuring Module and Insulin Pump Combination," U.S. Patent Publication No. 20040254434, filed Jun. 10, 2003, which is incorporated herein by reference in its entirety.

The controller 625 includes an insulin calculation module 630. The insulin calculation module 630 calculates a change in insulin therapy according to the activity information. The controller 625 then initiates delivery of the changed insulin therapy. The change to insulin therapy may include a change to a meal bolus or carbohydrate bolus, a change to a correction bolus, a change to a basal infusion of insulin (e.g., a basal insulin rate pattern or basal rate profile), or may include the insulin calculation module recommending that the user consume carbohydrates.

Figure 7:
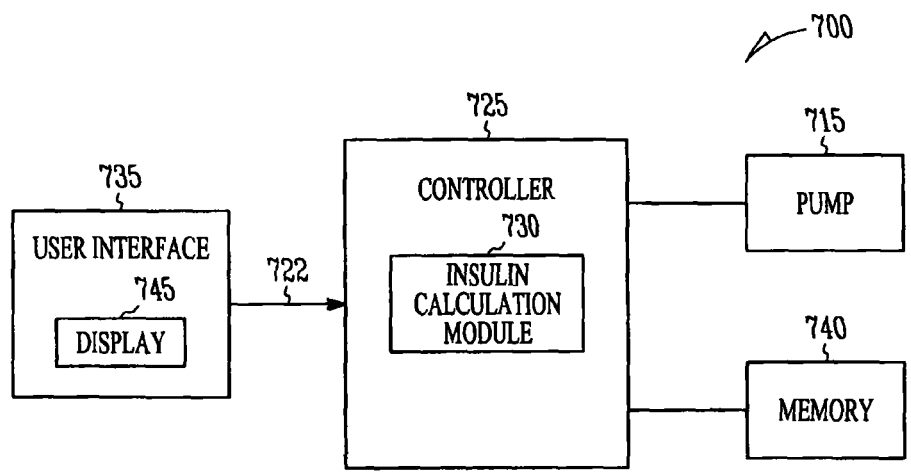
FIG. 7 is a block diagram of portions of another embodiment of a device that helps a user manage their blood glucose in response to activity.

FIG. 7 is a block diagram of portions of another embodiment of a device 700 that helps a user manage their blood glucose in response to activity. The device 700 includes a pump 715 configured to deliver insulin, an input 722, a controller 725, and an insulin calculation module 730 included in the controller 725. The device 700 also includes a user interface 735. Information related to exercise of the user is received by the controller 725 via the user interface 735.

The insulin calculation module 730 uses the exercise information to calculate an amount of carbohydrates metabolized by the exercise. In some embodiments, the insulin calculation module 730 estimates the amount of carbohydrates metabolized by the exercise according to a conversion rule. For example, the insulin calculation module 730 may estimate that the user metabolizes 15 to 30 grams every 30 to 60 minutes. The exact conversion rule can be tailored for the pump user and programmed into the controller 725 by the user or a diabetes professional. The conversion rule can be programmed via the user interface 735 or via a communication port 620 as shown in FIG. 6.

Figure 8:
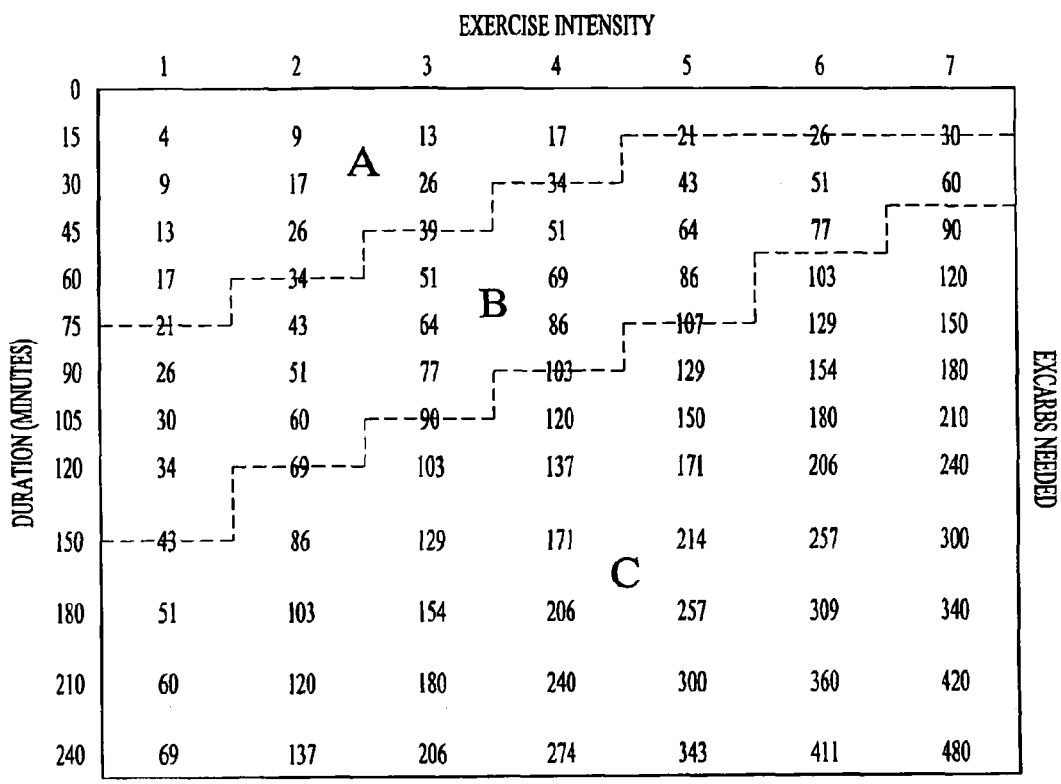
FIG. 8 shows an example of a table that indexes an amount of carbohydrates to an intensity and duration of exercise.

In some embodiments, the device 700 includes a memory 740. The conversion rule is a lookup table stored in the memory 740. The lookup table indexes the amount of carbohydrates metabolized according to the exercise intensity and the exercise duration. An exercise with a higher intensity (e.g., running) would have a higher intensity level and metabolize more carbohydrates than an exercise with a lower intensity (e.g., golfing). An example of a table that indexes an amount of carbohydrates to the intensity and duration of exercise is the ExCarbs Table published by Diabetes Services, Inc. and reproduced in FIG. 8. The intensity and duration of the exercise is entered via the user interface 735. In some examples, the table includes the amount of carbohydrates metabolized per amount of body weight (e.g., per 100 pounds). The insulin calculation module 730 calculates the amount of carbohydrates metabolized by the exercise from the user's body weight.

The insulin calculation module 730 calculates a reduction of an amount of insulin in a bolus by an amount that covers the metabolized amount of carbohydrates. In some examples, the insulin calculation module 730 calculates the reduction in insulin using a carbohydrate ratio stored in the device 700. A carbohydrate ratio refers to the amount of carbohydrates covered by a unit of insulin. It is sometimes referred to as a carbohydrate factor, or carb factor, and is typically specified as grams of carbohydrates per unit of insulin. The insulin calculation module 730 converts the amount of metabolized carbohydrates into an amount of insulin using the carbohydrate ratio and reduces the amount of insulin in a bolus by that amount. For example, the patient may metabolize seventy grams of carbohydrates during an exercise session. If the carbohydrate ratio is ten grams of carbohydrates per unit of insulin, the insulin pump may determine that seven units of insulin are required to cover the carbohydrates and reduce an amount of insulin in a bolus by seven units.

In some embodiments, the insulin calculation module 730 reduces the insulin in a meal bolus by an amount that covers the metabolized amount of carbohydrates. A meal bolus is an amount of insulin delivered in anticipation of, or in response to, eating a meal. In some examples, the insulin calculation module 730 reduces the insulin in a correction bolus. A correction bolus is a bolus of insulin designed to bring high blood glucose back to normal. In some examples, the insulin calculation module 730 reduces the insulin in a basal insulin rate pattern by an amount that covers the metabolized amount of carbohydrates. The insulin calculation module 730 temporarily reduces the rate of basal insulin delivery until the insulin reduction is covered and then restores the original rate of basal insulin delivery.

In some embodiments, the device 700 includes a display 745. After calculating an amount of carbohydrates metabolized by the exercise, the insulin calculation module 730 recommend, via the display, that the user consume the calculated amount of carbohydrates.

In some embodiments, one or more exercise regimens are stored in the memory 740. This is useful if the insulin pump user regularly repeats a type of exercise (e.g., regularly plays a round of golf at the same golf course or regularly runs a certain distance). An exercise regimen can be labeled "run" and can index a specified intensity and duration. The exercise intensity and duration may be used to determine the amount of metabolized carbohydrates, such as by using a lookup table as described previously. The exercise regimens may be received into the device 700 via the user interface 735, or may be received into the device 700 from a second separate device via a communication port.

The device 700 receives an indication, via the user interface 735, that the user will exercise according to a stored exercise regimen. In response to the received indication, the controller 725 presents on the display 745 an exercise insulin delivery pattern corresponding to the exercise regimen. In some examples, the exercise insulin delivery pattern is a basal insulin rate pattern that includes a reduction in insulin according to the carbohydrates metabolized during the exercise. The device receives, via the user interface, at least one of a selection of the exercise insulin delivery pattern into the device or a modification to the exercise insulin delivery pattern into the device. The controller 725 then initiates delivery of the selected or modified exercise insulin delivery pattern. The user may also cancel the exercise insulin delivery pattern via the user interface 735.

Figure 9:
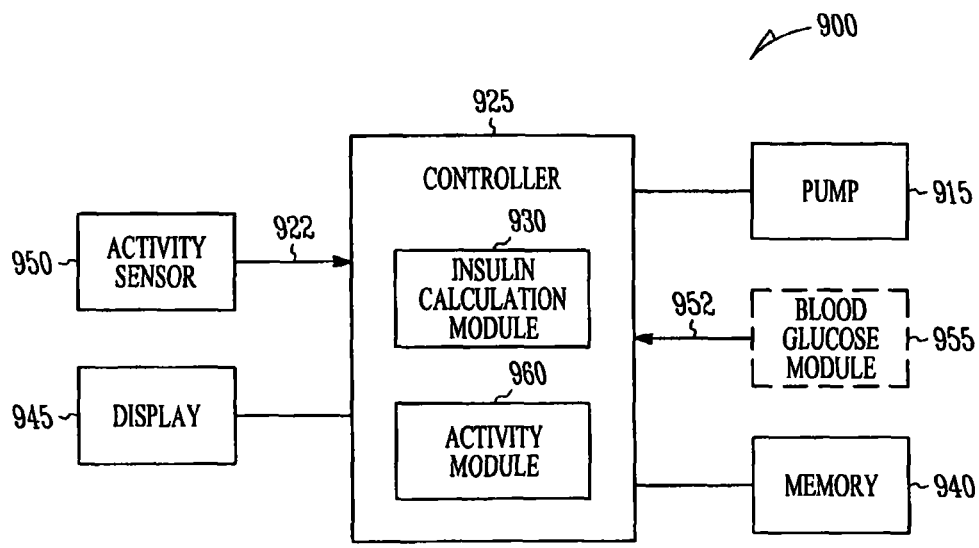
FIG. 9 is a block diagram of portions of still another embodiment of a device that helps a user manage their blood glucose in response to activity.

FIG. 9 is a block diagram of portions of still another embodiment of a device 900 that helps a user manage their blood glucose in response to activity. The device 900 includes a pump 915 configured to deliver insulin, an input 922, a controller 925, and an insulin calculation module 930 included in the controller 925. The device 900 includes an activity sensor 950 communicatively coupled to the input 922. The activity sensor 950 provides activity information in the form of an activity sensor signal that is an electrical signal representative of patient activity.

According to some embodiments, the device 900 includes a second input 952 and a display 945. The controller 925 receives information related to blood glucose into the insulin pump device via the second input and displays activity information in association with the blood glucose information on the device display 945. In certain embodiments, the controller 925 displays an indication of a period of high blood glucose level or a period of low blood glucose level on the device display 945 together with activity information. In certain embodiments, the controller 925 displays indications of both periods of high and low blood glucose levels together with an indication of activity level on the device display 945.

In some embodiments, the device 900 includes a user interface communicatively coupled to the second input 952. The controller 925 receives information related to blood glucose entered manually via the user interface.

In some embodiments, the device 900 includes a communication port communicatively coupled to the second input 952. The port may be a wired port or a wireless port. The controller 925 receives information related to blood glucose via the communication port from a second separate device. In some examples, the second device is a blood glucose monitor. In some embodiments, the second device is a blood glucose monitor included in an add-module to the device 900. In some embodiments, a blood glucose monitor 955 is integral to the device 900 and is communicatively coupled to the second input 952.

According to some embodiments, the device 900 includes a memory 940 and a display 945. The memory 940 stores a basal insulin rate pattern for an indicated activity level. For example, the memory 940 may store one basal rate pattern for an activity with an intensity level of "3" and a different basal rate pattern for an activity with an intensity level of "5". The controller 925 includes an activity module 960. The activity module 960 uses the activity sensor signal from the activity sensor 950 to determine an actual activity level of the patient during delivery of the basal insulin rate pattern, which may be different from the indicated activity level. The controller 925 displays an indication when the actual activity level deviates from the indicated activity level and displays a recommended change to the basal rate pattern.

In certain embodiments, if the actual level of exercise is less than the indicated level, the exercise basal rate pattern may not deliver enough insulin. The insulin calculation module 930 determines the difference between the actual carbohydrates metabolized and the amount of carbohydrates metabolized according to the stored indicated activity level and recommends an amount of insulin in a correction bolus to cover the difference. In certain embodiments, if the actual level of exercise is more than the indicated level, the exercise basal rate pattern may deliver too much insulin. The insulin calculation module determines the difference between the amount of carbohydrates covered by the insulin and the amount of carbohydrates metabolized, and the controller 925 displays an indication for the user to eat an amount of carbohydrates corresponding to the calculated difference.

In some embodiments, the activity module 960 establishes a baseline level of patient activity for a period of time. The period of time may be a period during the day when the pump user is more active, or may be a period of normal activity. In some examples, the activity module 960 establishes a baseline level for a specific activity (e.g., playing tennis).

In certain embodiments, the activity module 960 establishes a baseline activity level using a central tendency (e.g., an average value, or a median value) of the activity sensor signal. The activity module 960 then determines an actual level of patient activity during a time period (e.g., the time of day, or when the user indicates to the device 900 that they are playing tennis) using the activity sensor signal, and compares the actual level of patient activity to the baseline level. If the actual level of patient activity exceeds the baseline level by a threshold value, the insulin calculation module calculates and displays an amount of carbohydrates for the patient to consume.

If the actual level of patient activity is less than the baseline level by the same or a different threshold value, the controller 925 prompts the user, via the display 945, to initiate blood glucose tests more frequently. In certain embodiments, if the activity module 960 determines that the actual level of patient exercise is less than the baseline level by more than a threshold value, the insulin calculation module 930 calculates an amount of insulin to deliver in a correction bolus to bring the patient's blood glucose to a target level. The controller 925 may then display the recommended amount to the pump user who may then initiate the correction bolus through a user interface.

According to some embodiments, the memory 940 stores basal rate patterns in association with patient activity levels. For example, the memory 940 may store exercise basal rate patterns to be used during or after exercise. The activity module 960 determines a level of patient activity using the activity sensor signal. The controller 925 activates the exercise basal rate pattern according to the level of patient activity determined by the activity module 960. As an illustrative example, the memory 940 may store one basal rate pattern for normal activity, a first exercise basal rate pattern for an activity with an intensity level of "3", and a second exercise basal rate pattern for an activity with an intensity level of "5". When the activity module 960 determines that the activity level of the patient is "3", the controller 925 activates the first exercise basal rate pattern.

Other motion signatures in the activity sensor signal may provide other information to the device 900. For example, a sudden spike in the activity sensor signal may indicate that the device 900 underwent an impact. In some embodiments, the activity module 960 determines that the activity signal exceeds a signal threshold value associated with the insulin pump device undergoing an impact. In response to the determined impact, the controller displays a recommendation to check the insulin pump device, an insulin cartridge, or both the insulin pump device and insulin cartridge for damage.

Audio Capability

Because visual indications may be too difficult for a sight impaired pump user to see on a display, audible indications from an insulin pump may be desirable. Also, audio indications may be useful in attracting a non-sight impaired pump user's attention to the device in case of a pump-related alarm condition.

Figure 10:
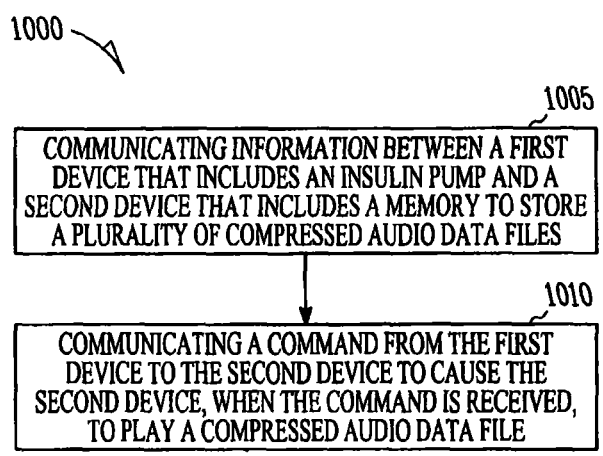
FIG. 10 is a flow diagram of an embodiment of a method of assisting an insulin pump user in managing their diabetes.

FIG. 10 is a flow diagram of a method 1000 of assisting an insulin pump user in managing their diabetes. At block 1005, information is communicated between a first device that includes an insulin pump and a second device that includes a memory to store a plurality of compressed audio data files. This includes at block 1010, communicating a command from the first device to the second device to cause the second device to play a compressed audio data file when the command is received. The audio data file may include an alert concerning the insulin pump device, or may include a status of the insulin pump device.

Figure 11:
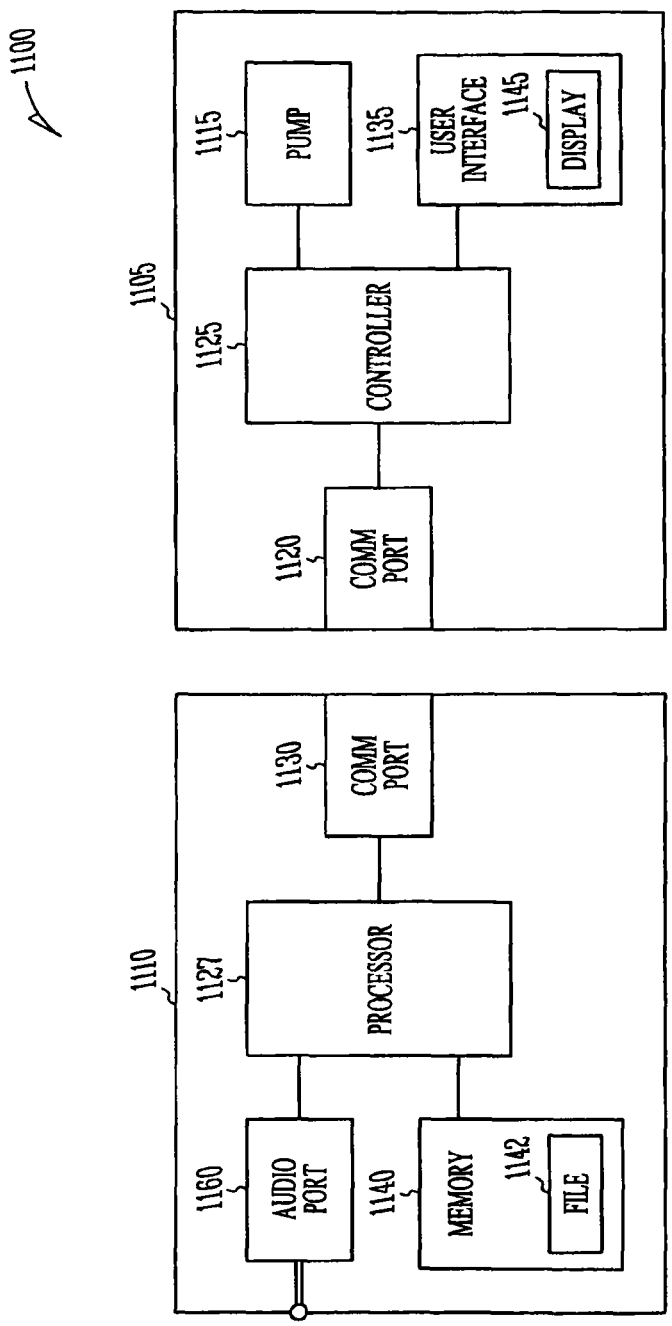
FIG. 11 is a block diagram of portions of an embodiment of a system that includes compressed audio files to assist an insulin pump user in managing their diabetes.

FIG. 11 is a block diagram of portions of an embodiment of a system 1100 that includes compressed audio files to assist an insulin pump user in managing their diabetes. The system 1100 includes a first device 1105 and a second device 1110. The first device includes a pump 1115 configured to deliver insulin, a communication port 1120, and a controller 1125 communicatively coupled to the pump 1115 and the communication port 1120. The controller 1125 communicates with the second device 1110 via the communication port 1120. The communication port 1120 may be a wired port or a wireless communication port.

The second device 1110 includes a processor 1127 and a memory 1140 integral to or communicatively coupled to the processor 1127. The memory 1140 stores one or more files of compressed audio data. In some embodiments, the compressed audio data file 1142 is compressed using a lossy compression algorithm, such as the MPEG-1 Audio Layer 3 (MP3) format for example. In some embodiments, the compressed audio data file 1142 is compressed using a lossless compression algorithm. The second device 1110 also includes a communication port 1130 and an audio port 1160. The communication port 1130 may be a wired port or a wireless communication port. In some embodiments, the second device 1110 is an add-on module that may be attached by any of the methods described or incorporated herein. In some embodiments, the second device 1110 includes a housing that includes a belt clip for wearing the second device 1110 with a belt. In certain embodiments, the communication ports are IR ports and the belt positions the second device 1110 for IR communication. The audio port 1160 may communicatively coupled to a speaker or to an audio jack, such as to receive an audio headphone connection for example.

The controller 1125 of the first device 1105 transmits a command to the second device 1110 to cause the second device 1110 to play the compressed audio data file 1142. In some examples, the command is communicated using an open standard wireless communication protocol. The processor 1127 of the second device 1110 receives the command and plays the compressed audio data file 1142 via the audio port 1160 in accordance with the command.

In some embodiments, the compressed audio file 1142 communicates an alert concerning the first device 1105 when played. In certain embodiments, the compressed audio file 1142 communicates an occlusion alarm when blockage tubing of the first device 1105 is detected. In certain embodiments, the compressed audio file 1142 communicates a status of the second device when played. Examples of status alerts include, among other things, that the device is currently running a test, details of insulin therapy provided by the device, and any insulin pump problems. Communicating audible alerts is useful to assist a sight impaired user of an insulin pump device.

In some embodiments, the compressed audio file 1142 communicates a result of a test run using the first device 1105. In certain embodiments, the controller 1125 may be configured to run a test to check operation of the pump 1115. In certain embodiments, the controller 1125 of the first device 1105 may be configured to calculate a carbohydrate ratio, to run a correction factor test, or to run a basal rate test.

As noted previously, a carbohydrate ratio refers to the amount of carbohydrates covered by a unit of insulin. Descriptions of devices and methods that perform a carbohydrate ratio test are found in Blomquist, "Carbohydrate Ratio Testing Using Frequent Blood Glucose Input," U.S. patent application Ser. No. 11/679,712, filed Feb. 27, 2007, which is incorporated herein by reference in its entirety. A correction factor refers to the amount in drop in blood sugar, or blood glucose, for one unit of insulin. Descriptions of devices and methods that perform a correction factor test are found in Blomquist et al., "Correction Factor Testing Using Frequent Blood Glucose Input," U.S. patent application Ser. No. 11/626,653, filed Jan. 24, 2007, which is incorporated herein by reference in its entirety. A basal rate test determines if a change should be made to a basal rate pattern. Descriptions of devices and methods that perform a basal rate test are found in Blomquist et al., "Basal Rate Testing Using Frequent Blood Glucose Input," U.S. patent application Ser. No. 11/685,617, filed Mar. 13, 2007, which is incorporated herein by reference in its entirety. After running such a test, the controller 1125 transmits a command to the second device 1110 to cause the second device 1110 to play a compressed audio data file 1142 regarding the test.

In some embodiments, the memory 1140 stores a plurality of compressed audio data files 1142 and the command indicates which audio data file to play. In some embodiments, the first device 1105 communicates a file of compressed audio data to the second device via the communication ports 1120, 1130. The second device 1110 then plays the communicated audio data file.

In some embodiments, the first device 1105 includes a user interface 1135 which includes a display 1145. The controller 1125 displays a menu containing a plurality of audio files (e.g., songs) playable on the second device 1110. The controller 1125 receives an audio file selection via the user interface 1135 and communicates a selected audio file option to the second device 1110 which plays the corresponding compressed audio data file 1142.

Temperature Monitoring

Figure 12:
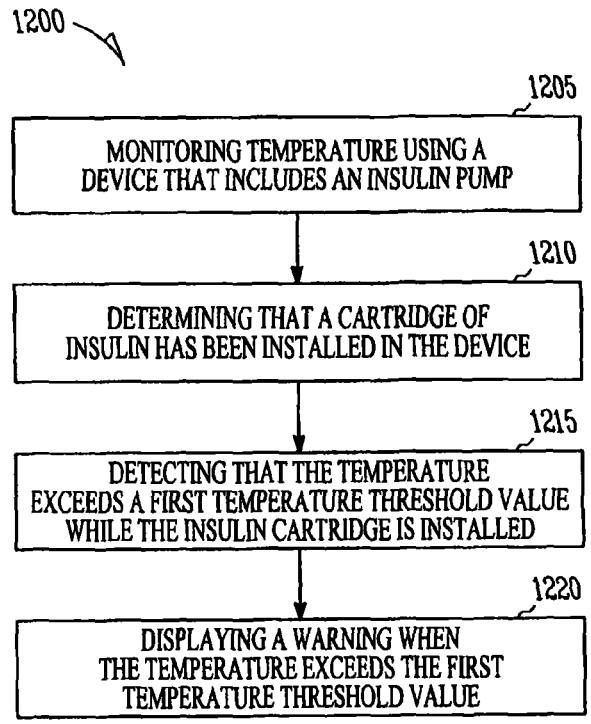
FIG. 12 is a flow diagram of an embodiment of a method to monitor insulin temperature.

Stability of insulin is impacted by temperature. Insulin may become bad if exposed to extremes of heat or cold. FIG. 12 is a flow diagram of an embodiment of a method 1200 to help an insulin pump user make best use of their pump. At block 1205, temperature is monitored using a device that includes an insulin pump. At block 1210, it is determined that a cartridge of insulin has been installed in the device. At block 1215, a temperature that exceeds a first temperature threshold value is detected while the insulin cartridge is installed. At block 1220, a warning is displayed when the temperature exceeds the first temperature threshold value.

Figure 13:
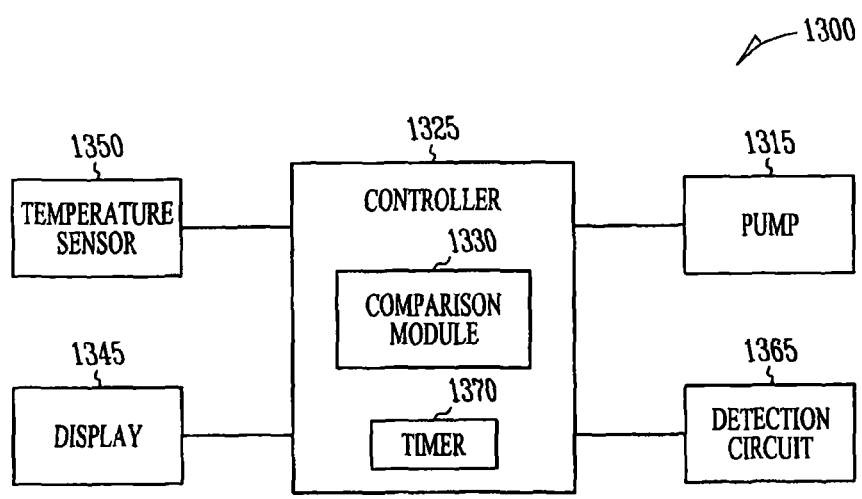
FIG. 13 is a block diagram of portions of a device to monitor temperature of insulin.

FIG. 13 is a block diagram of portions of a device 1300 to monitor temperature of insulin. The device 1300 includes a pump 1315 configured to deliver insulin and a detection circuit 1365 configured to detect when a cartridge of insulin is installed in the device 1300. In some embodiments, the detection circuit 1365 includes a switch (e.g., a button) that is activated when an insulin cartridge is inserted in the device 1300. The device 1300 also includes a temperature sensor 1350 that produces an electrical temperature signal representative of temperature, a display 1345, and a controller 1325. The controller 1325 is communicatively coupled to the pump 1315, the detection circuit 1365, and the temperature sensor 1350.

The controller 1325 includes a comparison module 1330 to detect when the temperature exceeds a first temperature threshold value while an insulin cartridge is installed. The controller 1325 displays a warning when the temperature exceeds the first temperature threshold value. In certain embodiments, the controller 1325 displays a warning that the insulin has been exposed to a high temperature, or displays a recommendation that the user initiate more frequent blood glucose readings. In some examples, the comparison module 1330 detects that the temperature is less than a second lower temperature threshold value while an insulin cartridge is installed. The controller 1325 then displays a warning that insulin has been exposed to a low temperature.

According to some embodiments, the temperature sensor 1350 monitors the temperature of the insulin cartridge. For example, the temperature sensor 1350 may be located proximate to or in contact with the insulin cartridge. The comparison module 1330 detects whether the temperature is below a second lower temperature threshold value. When the comparison module 1330 indicates that the temperature is below the second lower temperature threshold value, the controller 1325 displays a warning to check the insulin cartridge. In some embodiments, the comparison module 1330 detects when the temperature of the insulin cartridge rises from a temperature below the second temperature threshold to a temperature above the first temperature threshold. The controller 1325 then displays a recommendation that the user check for bubbles in the insulin cartridge.

Measuring a time-temperature product may provide a better indication of whether the insulin has been affected by temperature. According to some examples, the device 1300 includes a timer circuit 1370. The comparison module 1330 measures the temperature using the temperature signal from the temperature sensor 1350, and measures a duration of time that the measured temperature exceeds a threshold temperature value. The comparison module 1330 then determines a product of the measured time duration and the measured temperature, and detects when the product of the measured time duration and temperature exceed a threshold product value. If the product of measured time and temperature exceeds the threshold product value, the controller 1325 displays a warning, such as to check the insulin cartridge for bubbles or a warning that the time-temperature rating has been exceeded, for example.

Food Scale Interface

A meal bolus is an amount of insulin delivered in anticipation of, or in response to, eating a meal. Typically, the meal bolus insulin is to counteract or cover the amount the amount of carbohydrates in the meal. The proper amount of insulin can be influenced by many factors such as the nutrient content of the food in the meal. Nutrient content refers to the amount of carbohydrates, fiber, protein, and fat in the meal. Nutrient content may also include further indicate an amount of fast-absorbing carbohydrates in the meal. Determining an appropriate amount of insulin in the meal bolus can be difficult for a pump user due to difficulty in estimating the nutrient content of the food.

A food database contains the nutrient content for various types of food. The food database may include one or more food entries. A food database entry may include the nutrient content for a particular food (e.g., apple), and the database entries can be combined to determine the nutrient content of a meal (e.g., chicken, potato, green beans). An electronic food scale is helpful in determining the nutrient content of the meal. For example, the protein content of chicken per gram stored in the food database can be multiplied by the number of grams of chicken determined by the food scale. Estimating the amount of nutrient content in food would be easier for the insulin pump user if an electronic food scale communicated food information with an insulin pump. In some embodiments, the food data base is stored in the insulin pump and the insulin pump receives food weight information from the food scale. In some embodiments, the food database is stored in the food scale and the insulin pump receives food nutrient information from the food scale.

Figure 14:
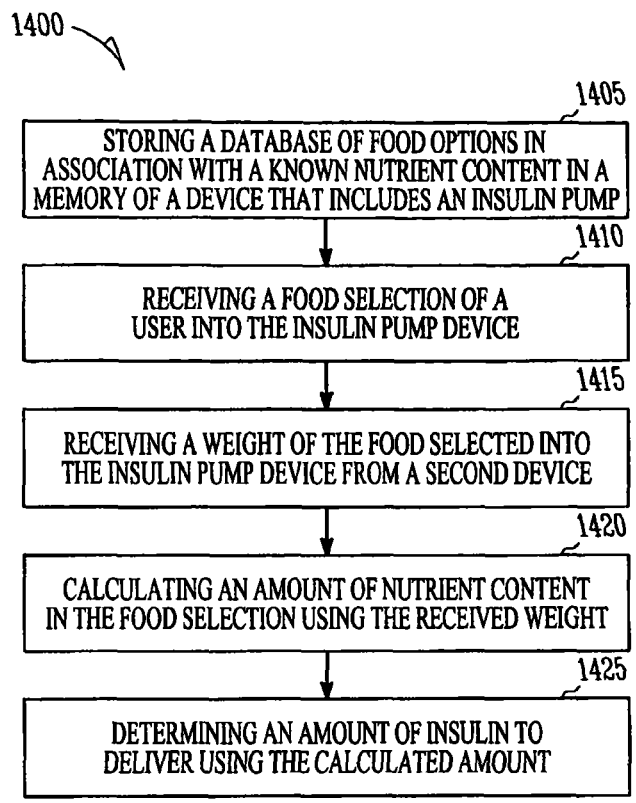
FIG. 14 is a flow diagram of an embodiment of a method of determining an amount of insulin to deliver in a bolus in response to a pump user ingesting a meal.

FIG. 14 is a flow diagram of an embodiment of a method 1400 of automatically determining an amount of insulin to deliver in a bolus in response to a pump user ingesting a meal (e.g., a meal bolus). At block 1405, a database of food options is stored in association with a known nutrient content in a memory of a device that includes an insulin pump. In some embodiments, a food database entry represents a food or a combination of foods. A food database entry may be stored as a record including the food name and the nutrient content of the food which includes at least one of the amounts of carbohydrates, fiber, protein, and fat in the food. The food database entries may be combined to determine the nutrient content for a meal. The food database entries may be programmed into the insulin pump device by the user or a diabetes professional, or the food entries may be downloaded into the insulin pump device from a separate device.

At block 1410, a food selection of a user is received into the insulin pump device, such as via a user interface for example. In some embodiments, selecting a food option includes scrolling through a list of food options which may be displayed using text or using a graphic of the food. At block 1415, receiving a weight of the food selected is received into the insulin pump device from a second device. In some embodiments, the second device includes a food scale.

At block 1420, the insulin pump device calculates an amount of nutrient content in the food selection using the received weight. At block 1425, an amount of insulin to deliver is determined using the calculated amount of nutrient content.

Figure 15:
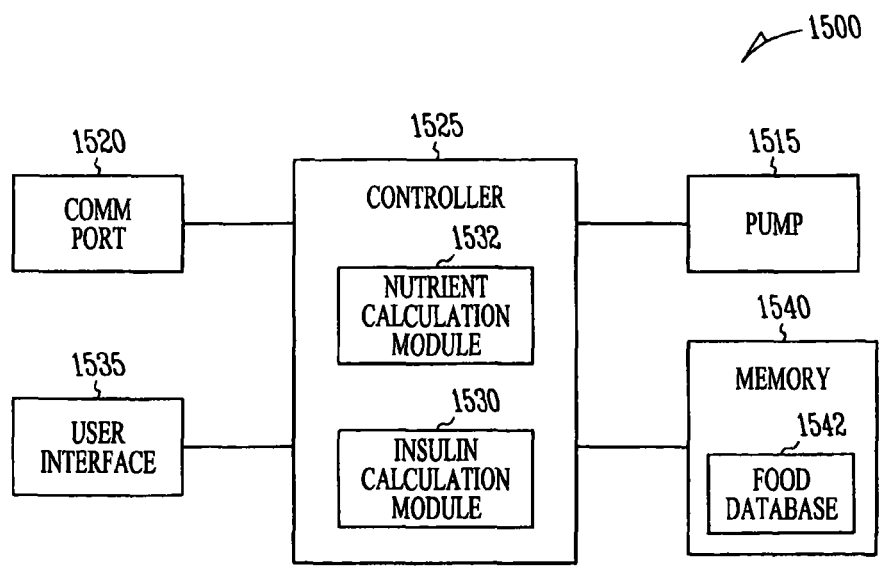
FIG. 15 is a block diagram of an embodiment of a device to determine an amount of insulin in an insulin bolus using food nutrient information.

FIG. 15 is a block diagram of an embodiment of a device 1500 to automatically determine an amount of insulin in an insulin bolus using food nutrient information. The device 1500 includes a pump 1515 configured to deliver insulin and a memory 1540 to store a food database 1542. In the food database 1542, food options are stored in association with a known amount of nutrient content. The device 1500 also includes a user interface 1535 configured to receive a food selection from a user, a communication port 1520, and a controller 1525. The communication 1520 may be a wired port or a wireless port.

The controller 1525 is communicatively coupled to the pump 1515, the memory 1540, the user interface 1535, and the communication port 1520. The controller 1525 receives, via the communication port 1520, a weight of the food selected into the insulin pump device from a second device (e.g., an electronic food scale). If the communication port 1520 is a wired port, the wired connection may be removable when not communicating information. The controller 1525 includes a nutrient calculation module 1532 that calculates an amount of nutrient content in the food selection using the received weight. For example, the food database 1542 may include the amount of at least one of carbohydrates, fiber, protein, or fat per gram of the food. The nutrient calculation module 1532 then multiplies the nutrient information by the received weight to determine the nutrient content of the meal.

The controller 1525 also includes an insulin calculation module 1530. The insulin calculation module 1530 determines an amount of insulin to deliver using the calculated amount. In some embodiments, the insulin calculation module 1530 uses at least one of a carbohydrate ratio, protein ratio, fat ratio, or fiber content to determine the amount of insulin to deliver. A carbohydrate ratio is sometimes referred to as a carbohydrate (or carb) factor and refers to the amount of carbohydrates covered by a unit of insulin. The insulin calculation module 1530 may use the carbohydrate ratio to automatically determine an amount of insulin required to match a number of carbohydrates ingested by the patient, or at least an amount required to keep post-meal blood glucose within a range that is healthy for a patient. For example, the nutrient information may indicate that the food the pump user plans to eat includes 70 grams of carbohydrates. If the carbohydrate ratio is 10 grams of carbohydrates per unit of insulin (10 g/u), the insulin pump determines that 7 units of insulin are required to cover the carbohydrates. Because fiber is considered a carbohydrate but not metabolized as a carbohydrate, the grams of fiber may be subtracted from the total grams of carbohydrates. Similar to a carbohydrate ratio, the insulin calculation module 1530 may use a protein ratio to determine an amount of insulin required to cover the protein in the meal, and/or a fat ratio to determine an amount of insulin required to cover the fat in the meal.

In some embodiments, the insulin is delivered as a meal bolus. In some embodiments, the insulin calculation module 1530 determines a change to a type of meal bolus using the calculated amount of nutrient content. For example, the nutrient content may indicate an amount of fast absorbing carbohydrates and an amount of slow absorbing carbohydrates. Based on the presence of fast and slow absorbing carbohydrates, the insulin calculation module 1530 may determine to deliver the insulin to cover the meal in a combination bolus.

Figure 16:
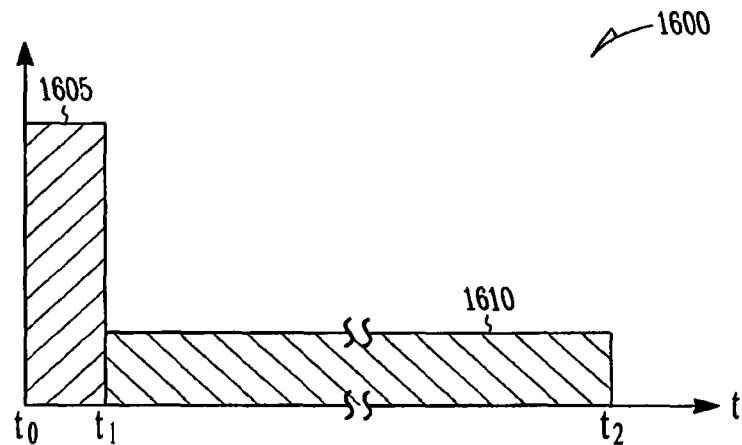
FIG. 16 illustrates a graph of an example of a combination bolus of insulin.

FIG. 16 illustrates a graph 1600 of an example of a combination bolus of insulin. The graph 1600 shows an amount of insulin delivered versus time. The combination meal bolus includes a first portion 1605 of insulin that is delivered immediately beginning at time $t_0$. The amount of insulin in the first portion 1605 may be determined using the amount of fast absorbing carbohydrates. The first portion 1605 concludes at time $t_1$ when a second portion 1610 of insulin begins to be delivered. The second portion 1610 is delivered over an extended period of time until time $t_2$. The extended portion is delivered at a lower rate and for a longer period of time than the first portion 1605. The amount of insulin in the second portion 1610 may be determined using the amount of slow absorbing carbohydrates.

Figure 17:
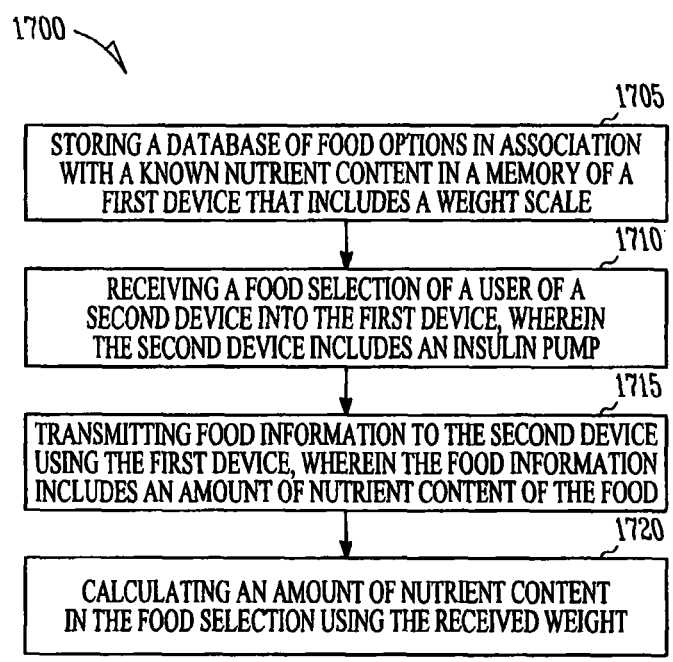
FIG. 17 is a flow diagram of another embodiment of a method of automatically determining an amount of insulin to deliver in a bolus.

FIG. 17 is a flow diagram of another embodiment of a method 1700 of automatically determining an amount of insulin to deliver in a bolus. At block 1705, a database of food options is stored in association with a known nutrient content in a memory of a first device that includes a weight scale (e.g., an electronic food weight scale). At block 1710, a food selection of a user of a second device is received into the first device. The second device includes the insulin pump.

At block 1715, food information is transmitted to the insulin pump device using the weight scale device. The food information includes an amount of nutrient content of the food. At block 1720, an amount of insulin to deliver by the insulin pump device is determined using the food information.

Figure 18:
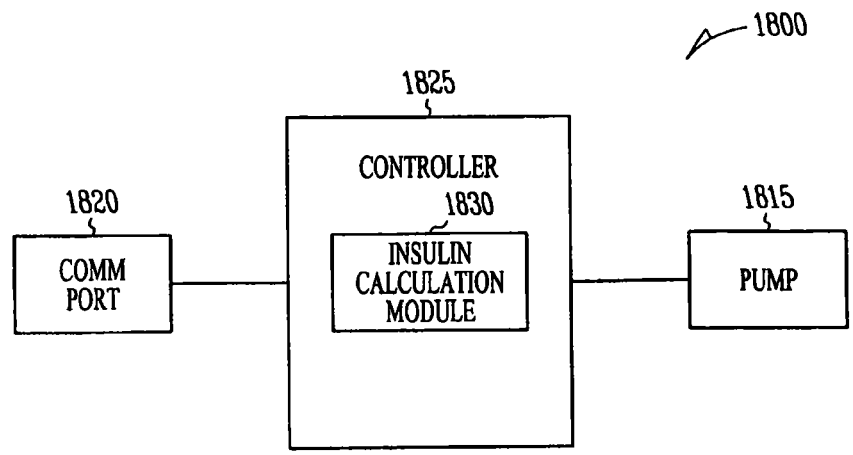
FIG. 18 is a block diagram of another embodiment of a device to automatically determine an amount of insulin in an insulin bolus using food nutrient information.

FIG. 18 is a block diagram of another example of a device 1800 to automatically determine an amount of insulin in an insulin bolus using food nutrient information. The device 1800 includes a pump 1815 configured to deliver insulin, a communication port 1820, and a controller 1825. The controller 1825 receives information regarding the nutrient content of food via the communication port 1820. The nutrient content is of food to be eaten by the pump user and the information is transmitted by a second device, such as a device that includes a weight scale for example. In certain embodiments, the communication port 1820 may be a wired port and the user connects the port when the information is to be communicated. In certain embodiments, the communication port 1820 is a wireless communication port.

The controller 1825 includes an insulin calculation module 1830 that determines an amount of insulin to deliver, in anticipation of the user eating the meal, using the nutrient content information received into the device 1800. In some embodiments, the insulin is delivered as a meal bolus. In some embodiments, the insulin calculation module determines, using the nutrient content, whether the meal bolus should include an extended bolus. In certain examples, the extended bolus is included in a combination bolus, such as the illustrative example shown in FIG. 16. The second portion 1610 of the combination bolus is an extended bolus.

Personal Information Manager Feature

Information related to the daily routine of an insulin pump user is often in electronic form. For example, the user may have a personal information manager (PIM) device, such as a personal data assistant (PDA) or the like. Information related to daily events of the user is stored in the device using an interactive calendar. This information may useful in setting or adjusting insulin therapy from an insulin pump.

Figure 19:
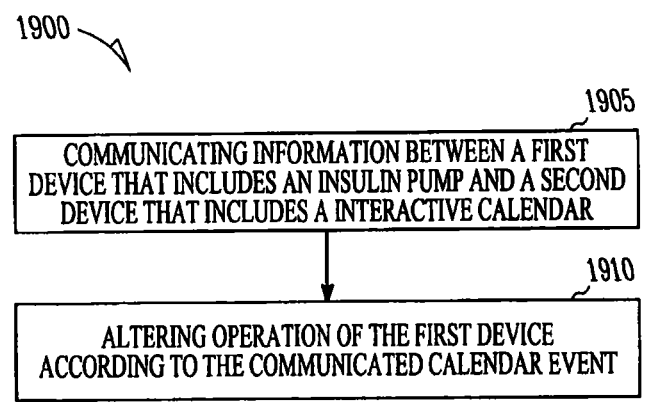
FIG. 19 shows a flow diagram of an embodiment of a method to program an insulin pump device using an interactive calendar.

FIG. 19 shows a flow diagram of an embodiment of a method 1900 to program an insulin pump device using an interactive calendar. At block 1905, information is communicated between a first device that includes an insulin pump and a second device that includes an interactive calendar. In some embodiments, the second device is an add-on module to the insulin pump device. In some embodiments, the second device is a separate device (e.g., a PDA or any computing device running an interactive calendar program). The information communicated between the two devices includes a calendar event of a user of the first device entered into the interactive calendar of the second device.

At block 1910, operation of the first device is altered according to the communicated calendar event. Examples of altering operation if the first device include, among other things, changing a delivery of insulin, activating an exercise basal rate pattern, and changing an alarm mode of the first device.

Figure 20:
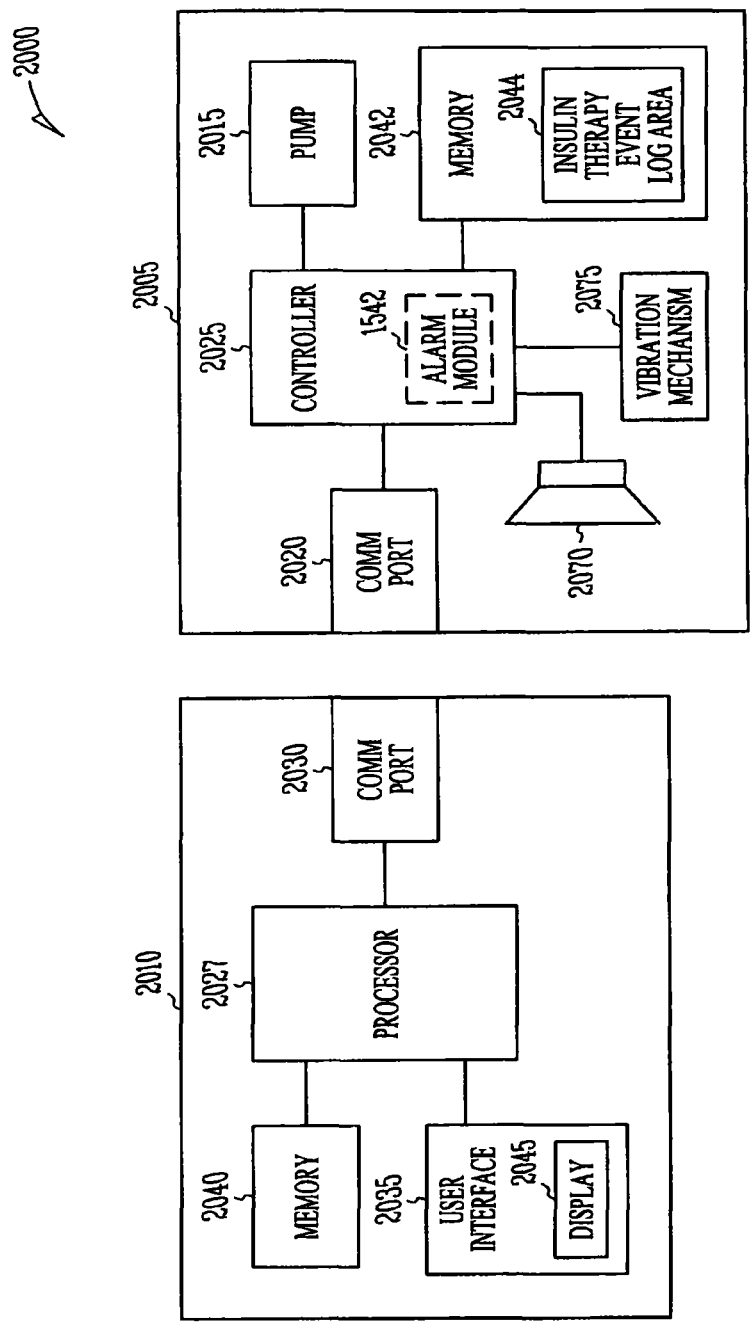
FIG. 20 is a block diagram of portions of an embodiment of a system that includes an insulin pump device.

FIG. 20 is a block diagram of portions of a system 2000 that includes an insulin pump device. The system 2000 includes a first device 2005 and a second device 2010. The first device 2005 is an insulin pump device and includes the pump 2015, a first communication port 2020, and a controller 2025 that initiates insulin therapy delivered by the pump 2015.

The second device 2010 implements an interactive calendar and includes a memory 2040 to store a plurality of calendar events of a user, a user interface 2035 including a display 2045, a second communication port 2030, and a processor 2027. The user interface 2035 receives a calendar event into the memory 2040 of the second device 2010 and the processor 2027 displays the calendar event. The processor 2027 is configured to communicate information to the first device 2005 using the second communication port 2030. The communicated information includes a calendar event of the user. The controller 2025 of the first device 2005 alters operation of the first device according to the communicated calendar event.

According to some embodiments, the communicated calendar event includes a meal time of the user. The controller 2025 schedules a missed meal bolus alarm in a time relation to the meal time (e.g., a specified time duration after the scheduled meal time). If the user fails to initiate a meal bolus using the first device 2005, the controller 2025 generates a missed meal bolus alarm, or other kind of alert to the user. The user may then initiate the meal bolus if they did indeed eat and forgot to initiate a meal bolus, or may merely cancel the alarm if they did not eat at the scheduled time.

According to some embodiments, the communicated calendar event includes an exercise time. In some embodiments, the exercise time is when the user exercises according to a specified exercise regimen (e.g., walking a specified distance). The controller 2025 of the insulin pump device changes a delivery of insulin in relation to the communicated exercise time. For example, the controller 2025 may automatically change the basal rate pattern delivered by the device to an exercise basal rate pattern or profile that corresponds to the specified exercise. The controller 2025 changes to the exercise basal pattern in relation to the communicated exercise time (e.g., a specified time duration before the exercise regimen begins, as the regimen is scheduled to begin, or a time duration after the exercise regimen begins). In some examples, the first device 2005 includes a display and displays a prompt as to whether the user wishes to activate the exercise basal rate pattern. The user may then enable or cancel activation of the exercise basal rate pattern.

In some embodiments, the controller 2025 calculates an amount of carbohydrates metabolized by the specified exercise regimen and reduces an amount of insulin to be delivered by the first device 2005 by an amount that covers the metabolized carbohydrates. Examples of devices that calculate carbohydrates metabolized by exercise were described previously in regard to FIG. 7.

The first device 2005 may include an audible indicator 2070 and a vibration mechanism 2075 communicatively coupled to the controller 2025. An example of an audible indicator 2070 is a transducer or speaker. The controller 2025 may include an alarm module 2032 to generate an audible alert, such as a reminder to initiate a meal bolus or a reminder to take a blood glucose measurement for example. The alarm module 2032 generates a vibratory alert for such reminders using the vibration mechanism 2075. In some embodiments, the communicated calendar event includes a meeting time and, according to the meeting time, the alarm module 2032 switches an alarm mode of the first device 2005 between an audible mode and a vibratory mode according to the communicated meeting time. Thus, the alarm module 2032 automatically switches from the audible alert to a silent alert during the meeting time, and may switch back from the silent alert to the audible alert after the meeting time.

According to some examples, the first device 2005 includes a memory 2042 coupled to or integral to the controller 2025. The memory 2042 includes an insulin therapy event log memory area 2044. The controller 2025 stores an event related to insulin therapy in association with the communicated calendar event as a log entry in the insulin therapy event log memory area 2044. Storing an insulin therapy event in association with the communicated calendar event is useful to provide context to insulin therapy events such as blood glucose readings or pump deliveries of insulin. In some examples, the controller 2025 generates a report that includes one or more log entries from the insulin therapy event log memory area 2044. The report may be displayed via a display included in the first device 2005, or the report may be communicated via the communication port to the second device 2010 or a third device for display or printing. The generated report may be useful in making decisions concerning adjustment to insulin therapy provided by the insulin pump device.

Speech Recognition

In some situations it may be desirable to communicate with an insulin pump device without the need to navigate operational menus displayed on the insulin pump device. For example, the pump user may be visually impaired. For this reason, it is desirable to provide speech recognition capability in an insulin pump device.

Figure 21:
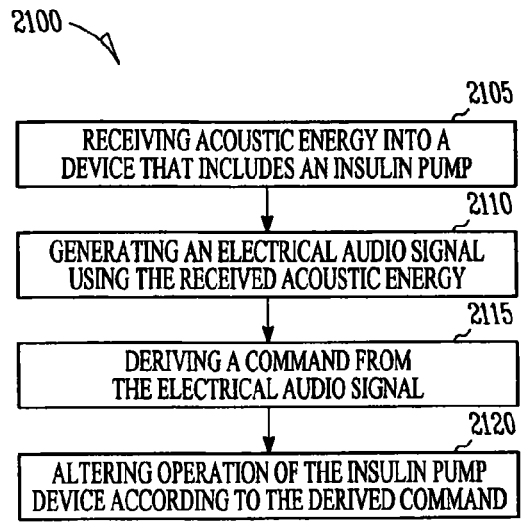
FIG. 21 is a flow diagram of an embodiment of a method of operating an insulin pump device.

FIG. 21 is a flow diagram of an embodiment of a method 2100 of operating an insulin pump device. At block 2105, acoustic energy is received into a device that includes an insulin pump. Typically, the acoustic energy is radiated from speech of the insulin pump user. At block 2110, an electrical audio signal is generated by the insulin pump device using the received acoustic energy. At block 2115, a command is derived from the electrical audio signal. At block 2135, altering operation of the insulin pump device is altered according to the derived command. For example, the command may be, among other things, a command to initiate or change a delivery of insulin from the insulin pump device, to run a device test, or to change an operating parameter of the device.

Figure 22:
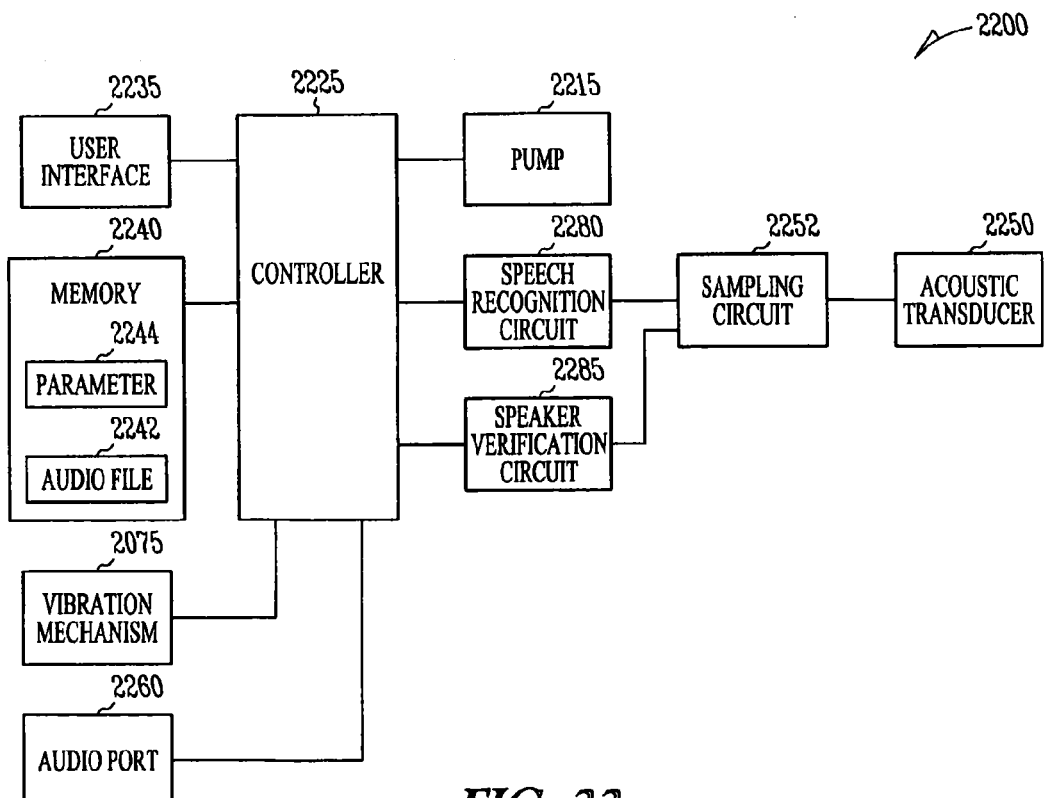
FIG. 22 is a block diagram of portions of an embodiment of a device to provide voice control of insulin therapy.

FIG. 22 is a block diagram of portions of a device 2200 to provide voice control of insulin therapy. The device 2200 includes a pump 2215 configured to deliver insulin, an acoustic transducer 2250, a speech recognition circuit 2280, and a controller 2225. The acoustic transducer 2250 receives acoustic energy and generates an electrical transducer signal representative of the acoustic energy. An example of an acoustic transducer is a microphone. The acoustic energy is typically generated from speech of the pump user or another person interacting with the device 2200. The device may include a transducer interface circuit such as a sampling circuit 2252 that produces digitized samples of the electrical transducer signal. The speech recognition circuit 2280 derives a command from the digitized samples. In some embodiments, the speech recognition circuit 2280 includes digital signal processing circuitry to derive the command. In some embodiments, the acoustic transducer 2250, the transducer interface circuit, and the speech recognition circuit 2280 are included in an add-on module. The add-on module may include a second processor, such as a digital signal processor (DSP), coupled to the speech recognition circuit 2280 to derive the command and a communication port to communicate a derived command to the controller 2225.

The controller 2225 alters operation of the device 2200 according to the derived command. In some embodiments, the command derived by the speech recognition circuit 2280 from the electrical transducer signal is to initiate delivery of a correction bolus of insulin. In some embodiments, the command derived by the speech recognition circuit 2280 from the electrical transducer signal is to initiate delivery of a meal bolus of insulin. The controller 2225 then initiates delivery of the correction bolus or meal bolus according to the derived command.

In some embodiments, the command derived by the speech recognition circuit 2280 is to change a basal insulin rate pattern or basal rate profile. In certain embodiments, the device 2200 may include a memory 2240 that stores a plurality of basal rate patterns. The derived command may be to activate a different basal rate pattern than the basal rate pattern that is currently active. For example, the memory 2240 may store different basal rate patterns for different activity levels of the pump user. The pump user may speak a command to activate an exercise basal rate pattern, and the speech recognition circuit 2280 derives the user's command. In some embodiments, the speech recognition circuit 2280 derives a command to deactivate insulin pump therapy and controller 2225 deactivates the therapy provided by the pump when the command is derived. This deactivation may be implemented as an emergency shut-off command.

According to some embodiments, the controller 2225 runs one or more device-based tests. The speech recognition circuit 2280 is configured to derive a command to run a device test, and the controller 2225 is configured to initiate the test according to the command. In certain embodiments, the controller 2225 is configured to execute a device diagnostic test. In certain embodiments, the controller 2225 is configured to execute a carbohydrate ratio test. Descriptions of devices and methods that perform a carbohydrate ratio test are found in the previously mentioned U.S. patent application Ser. No. 11/679,712. In certain embodiments, the controller 2225 is configured to execute a correction factor test. Descriptions of devices and methods that perform a correction factor test are found in the previously mentioned U.S. patent application Ser. No. 11/626,653. In certain embodiments, the controller 2225 is configured to execute a basal rate test. Descriptions of devices and methods that perform a basal rate test are found in the previously mentioned U.S. patent application Ser. No. 11/685,617. The controller 2225 runs the carbohydrate ratio test, the correction factor test, or the basal rate test according to the derived command.

According to some embodiments, at least one operating parameter 2244 of the device 2200 is stored in the memory 2240. The speech recognition circuit 2280 derives a command from the transducer signal to change the operating parameter 2244 of the device 2200. The controller 2225 updates the operating parameter 2244 in the memory 2240 in response to the derived command. In certain embodiments, the operating parameter is a correction factor. The pump user speaks a command to update the correction factor to a specified value. The speech recognition circuit 2280 derives the command to change the correction factor and derives the specified value of the correction factor from the transducer signal. The controller 2225 updates the correction factor in memory 2240.

In certain embodiments, the operating parameter is a carbohydrate ratio. The pump user speaks a command to update the carbohydrate ratio to a specified value. The speech recognition circuit 2280 derives the command to change the carbohydrate ratio and derives the specified value of carbohydrate ratio from the transducer signal. The controller 2225 updates the carbohydrate ratio in memory 2240.

It may be desirable to enable operation of the device 2200 with speech recognition only during certain times. This may help avoid inadvertent changes to operation of the device 2200. In some embodiments, the speech recognition feature must be enabled on the device 2200 before use. The device 2200 includes a user interface 2235 communicatively coupled to the controller 2225. The controller 2225 deactivates processing of audio signals until an activation signal is received via the user interface 2235. The processing of audio signals continues until a deactivation signal is received via the user interface 2235.

Ambient noise may make it difficult for the speech recognition feature to derive commands from speech. In some embodiments, the device 2200 includes a vibration mechanism 2075 communicatively coupled to the controller 2225. The speech recognition circuit 2280 generates an indication when ambient noise prevents speech recognition from the digitized samples. For example, the speech recognition circuit 2280 may detect that ambient noise is above a threshold ambient noise level. When the controller 2225 receives such an indication from the speech recognition circuit, the controller 2225 provides a vibratory alert using the vibratory mechanism. Thus, the device 2200 alerts the user when speech recognition may not be usable.

It may be desirable to add a measure of security in using the speech recognition feature. In some embodiments, operation of the device 2200 by speech recognition is enabled by a specified password. The speech recognition circuit 2280 derives a message corresponding to a spoken password from the digitized samples from the sampling circuit 2252. The controller 2225 deactivates altering operation of the device according to a derived command until the message with the password is derived. Thus, speech recognition is active, but commands to alter operation of the device are not derived until the password is detected.

In some embodiments, operation of the device 2200 by speech recognition is only allowed when the device 2200 verifies the speaker is the insulin pump user. This is referred to as voice recognition or speaker verification. In some embodiments, the device 2200 includes a speaker verification circuit 2285 communicatively coupled to the sampling circuit 2252 and the controller 2225. The speak verification circuit is configured to verify that the digitized samples from the sampling circuit 2252 correlate to a pump user's voice. The controller alters operation of the device 2200 using the derived command from the speech recognition circuit 2280 only when the speaker verification circuit 2285 also verifies that the command came from the user's voice. In certain embodiments, the speaker verification circuit 2285 includes a DSP. In certain embodiments, the speaker verification circuit 2285 executes adaptive learning to recognize the pump user's voice.

According to some embodiments, voice operation of the insulin pump device includes outputting recorded voice prompts to the insulin pump user. In some embodiments, the memory 2240 stores one or more files of compressed audio data. The device 2200 includes an audio port 2260 communicatively coupled to the controller 2225. The audio port 2260 may be coupled to a speaker or to an audio jack to receive headphones. The controller 2225 plays the compressed audio data file via the audio port 2260. For example, the controller 2225 may play a compressed audio data file to ask the user whether they want to initiate a meal bolus. This may be played as part of a meal bolus reminder. The controller initiates the meal bolus when the speech recognition circuit 2280 derives the word "yes" from the user, and does not initiate the meal bolus if the speech recognition circuit 2280 derives the word "no" from the user. Other compressed data files may be played to provide alarms or alerts to the user, to inquire whether the user wants to run a device test, or to provide an acknowledge message to the pump user that a command from the user was derived and executed.

Kinetic Battery

Figure 23:
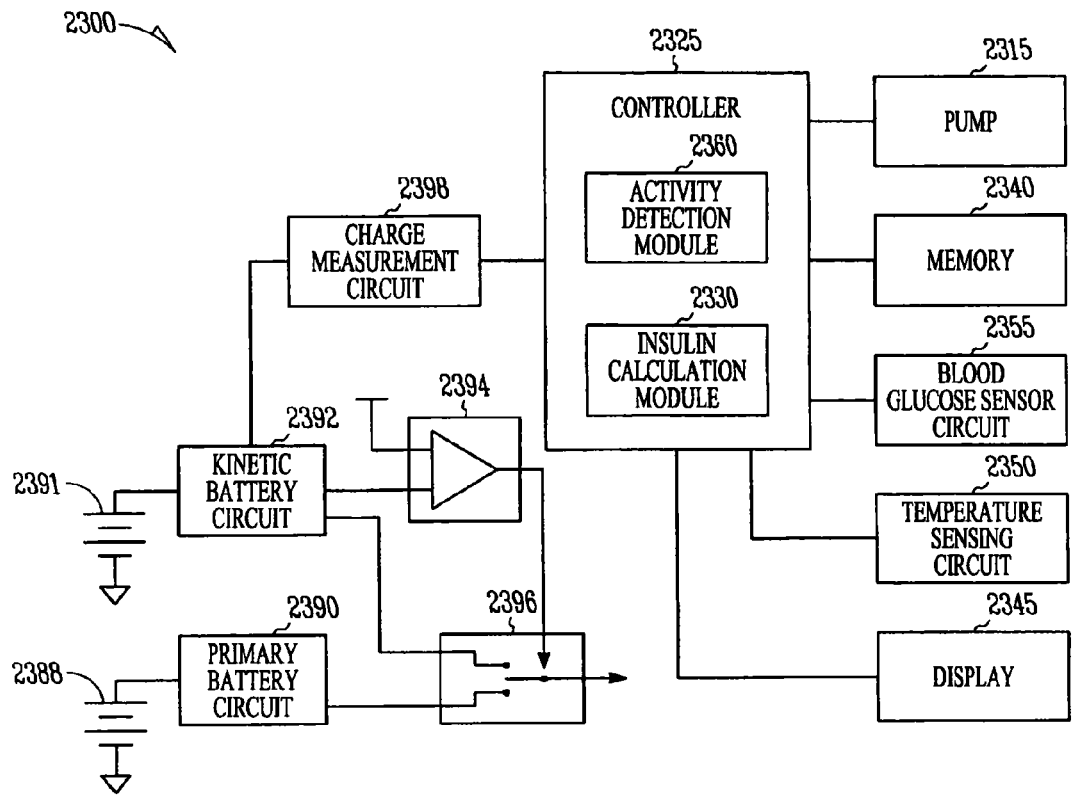
FIG. 23 is block diagram of portions of an embodiment of a device to provide insulin therapy.

Insulin pumps are typically battery powered devices. It may desirable to extend the battery life of an insulin pump device. FIG. 23 is block diagram of portions of an embodiment of a device 2300 to provide insulin therapy. The device 2300 includes a pump 2315 configured to deliver insulin and a controller 2325 to initiate delivery of insulin therapy from the pump 2315. The device 2300 also includes a primary battery circuit 2390 and a kinetic battery circuit 2392. The primary battery circuit 2390 provides energy to the device 2300 from a primary battery 2388. The kinetic battery circuit 2392 provides energy to at least a portion of the device 2300 from a kinetic battery 2391. The kinetic battery circuit 2392 also converts motion of a user to charge stored in a kinetic battery 2391, such as by using moving magnets to create electrical energy in coils of wire.

The device 2300 further includes a comparison circuit 2394 and a switching circuit 2396. The switching circuit 2396 switches the power source of at least of a portion of the device 2300 between the primary battery circuit 2390 and the kinetic battery circuit 2392. The comparison circuit 2394 compares a charge on the kinetic battery 2391 to a threshold charge value. When the comparison circuit 2394 detects that the charge on the kinetic battery 2391 exceeds the threshold, the switching circuit 2396 provides energy from the kinetic battery circuit 2392 to at least a portion of the device 2300. When the charge on the kinetic battery 2391 is less than the threshold, the switching circuit 2396 provides energy to the portion from the primary battery circuit 2390. In some embodiments, the kinetic battery circuit 2392 and kinetic battery 2391 are included in an add-on module that is connected to the switching circuit 2396.

According to some examples, because the kinetic battery circuit 2392 converts movement of the pump user into battery energy, the kinetic battery circuit 2392 can be used to detect user activity. In some embodiments, the device 2300 includes a charge measurement circuit 2398 communicatively coupled to the kinetic battery circuit and the controller, which is configured to measure a level of charge on the kinetic battery 2391. The controller 2325 includes an activity detection module 2360 configured to determine an activity level of the user from the measured level of charge. For example, the activity detection module 2360 may store a first value $Q_1$ representing a level of charge on the kinetic battery at time $t_1$. At a later time, $t_2$, the activity detection module 2360 may determine that the charge on the kinetic battery has increased to a second value $Q_2$ during the time period from time $t_1$ to $t_2$. The activity detection module 2360 may detect that the activity level of the user is increasing from the increase in charge.

In some embodiments, the activity detection module 2360 may determine the activity level of the user from the difference between the first value of charge and the second value of charge (e.g., $Q_2-Q_1$). In certain embodiments, the charge measurement circuit 2398 is configured to measure a rate of change of the charge on the kinetic battery 2391. The activity detection module 2360 determines the activity level of the user using the measured rate of change of the charge.

For example, the activity detection module 2360 may determine the rate of change by dividing the difference in charge values by the difference in time, or $$\frac{Q_2-Q_1}{t_2-t_1}.$$

Larger values for the rate of change indicate a higher activity level of the pump user.

In some embodiments, the controller 2325 includes an insulin calculation module 2330 that calculates a change in a delivery of insulin according to the indicated activity level. The calculated change to insulin therapy may include a calculated reduction in an amount of insulin in at least one of a correction bolus, a meal bolus, or a basal insulin rate pattern according to the activity level. As discussed previously in regard to FIGS. 6 and 7, the insulin calculation module 2330 uses the activity level to calculate an amount of carbohydrates metabolized by the exercise, such as by using a conversion rule for example. The insulin calculation module 2330 then calculates a reduction of an amount of insulin by an amount that covers the metabolized amount of carbohydrates.

In some embodiments, the device 2300 includes a memory 2340 that may be integral to the controller 2325 or communicatively coupled to the controller 2325. The memory 2340 stores an exercise basal rate pattern. The controller 2325 activates the exercise basal rate pattern according to the indicated activity level.

The kinetic battery circuit 2392 may be used to provide energy to the entire device 2300 or to portions of the device 2300. In some embodiments, the device 2300 includes a blood glucose sensor circuit 2355 to produce an electrical blood glucose signal representative of a blood glucose level of the patient. The switching circuit 2396 provides energy to the blood glucose sensor circuit 2355 from the kinetic battery 2391 when the charge on the kinetic battery 2391 exceeds the threshold charge value. In some embodiments, the device 2300 includes a temperature sensing circuit 2350 that produces an electrical temperature signal representative of temperature. The switching circuit 2396 provides energy to the temperature sensing circuit 2350 from the kinetic battery 2391 when the charge on the kinetic battery 2391 exceeds the threshold charge value. In some embodiments, the device 2300 includes a display 2345. The switching circuit 2396 provides energy to the display 2345 from the kinetic battery 2391 when the charge on the kinetic battery 2391 exceeds the threshold charge value.

Figure 24:
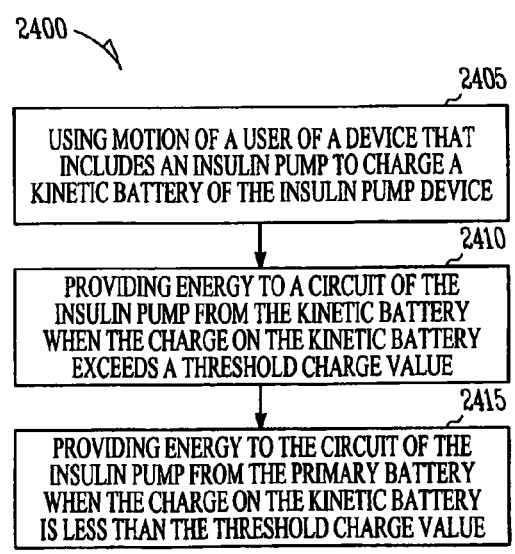
FIG. 24 is a flow diagram of an embodiment of a method of extending the battery life of an insulin pump.

FIG. 24 is a flow diagram of an embodiment of a method 2400 of extending the primary battery life of an insulin pump. At block 2405, motion of a user of a device that includes an insulin pump is used to charge a kinetic battery of the insulin pump device. At block 2410, energy is provided to a circuit of the insulin pump device from the kinetic battery when the charge on the kinetic battery exceeds a threshold charge value. At block 2415, energy is provided to the circuit of the insulin pump from the primary battery when the charge on the kinetic battery is less than the threshold charge value.

The above detailed description includes references to the accompanying drawings, which form a part of the detailed description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

It is to be understood that the above description is intended to be illustrative, and not restrictive. For example, the above-described embodiments (and/or aspects thereof) may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects. In this document, the terms "a" or "an" are used, as is common in patent documents, to include one or more than one. In this document, the term "or" is used to refer to a nonexclusive or, such that "A or B" includes "A but not B," "B but not A," and "A and B," unless otherwise indicated.

The Abstract is provided to comply with 37 C.F.R. §1.72 (b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

The invention claimed is:
1. An apparatus comprising:
a pump configured to deliver a fluid;
a wireless communication port;
a controller communicatively coupled to the pump and the communication port, wherein the controller is configured to control and operate the pump and to communicate with a second device via the communication port using an open standard wireless communication protocol; and
a housing to enclose the pump and the controller to form a pump device capable of independently delivering the fluid to a user, wherein the housing includes a mechanical coupling to slidably mechanically engage the second device which includes a second wireless communication port, and wherein slidably engaging the second device positions the first and second communication ports opposite each other to allow communication of information between the second device and the controller via the first and second communication ports when slidably engaged, wherein the second device provides an enhanced capability to the apparatus when mechanically engaged with said housing and communicatively engaged with said controller.

2. The apparatus of claim 1, wherein the mechanical coupling includes a locking mechanism to lock the second device in the slidably engaged position, and wherein the second device includes a release mechanism to release the second device from the slidably engaged position.

3. The apparatus of claim 1, wherein the communication port is an infrared communication port.

4. The apparatus of claim 1, wherein the communication port is a radio communication port.

5. The apparatus of claim 1, wherein the pump is an infusion pump having infusion tubing configured to be connected to a patient to deliver the fluid to the patient, and the enhanced capability provided by the second device is monitoring a physical parameter of the patient.

6. A method of expanding functional capability of a device that includes an infusion pump, the method comprising:
positioning a mechanical coupling on a housing that encloses the pump device, wherein the mechanical coupling slidably engages a second device, the pump device including a pump and a controller within the housing capable of independently controlling the pump to deliver a fluid to a user;
positioning a first wireless communication port of the housing in relation to the mechanical coupling such that, when the second device is in a slidably engaged position, the first wireless communication port is positioned opposite a second wireless communication port of the second device; and
communicating information with the second device via the first communication port of the housing and the second communication port of the second device using an open standard wireless communication protocol to cause the second device to provide an enhanced capability to the device.

7. The method of claim 6 including:
slidably engaging the second device until a locking mechanism included in the mechanical coupling locks the second apparatus in the slidably engaged position; and
detaching the second device from the slidably engaged position using a release mechanism.

8. The method of claim 6, wherein positioning a wireless communication port includes positioning an infrared communication port.

9. The method of claim 6, wherein positioning a wireless communication port includes positioning a radio communication port.

10. The method of claim 6, wherein the infusion pump includes infusion tubing that delivers a fluid to a patient, and the second device providing an enhanced capability to the device includes monitoring a physical parameter of a patient.

11. The apparatus of claim 5, wherein the physical parameter is a blood glucose level.

12. The apparatus of claim 5, wherein the physical parameter is an activity level.

13. The apparatus of claim 1, wherein the enhanced capability provided by the second device is testing a patient's blood.

14. The method of claim 10, wherein monitoring a physical parameter of a patient includes monitoring a blood glucose level of the patient.

15. The method of claim 10, wherein monitoring a physical parameter of a patient includes monitoring an activity level of the patient.

16. The method of claim 6, the second device providing an enhanced capability to the device includes testing a patient's blood.

17. The apparatus of claim 1, wherein the second device does not control or send commands to control the pump in delivering the fluid to the user.

18. The method of claim 1, wherein the second device is not used to control or send commands to control the pump in delivering the fluid to the user.

\* \* \* \* \*

UNITED STATES PATENT AND TRADEMARK OFFICE
CERTIFICATE OF CORRECTION

Page 1 of 1

| | |
|---|---|
| PATENT NO. | : 8,414,523 B2 |
| APPLICATION NO. | : 12/914295 |
| DATED | : April 9, 2013 |
| INVENTOR(S) | : Blomquist et al. |

It is certified that error appears in the above-identified patent and that said Letters Patent is hereby corrected as shown below:

In The Specification

Column 3, Line 65:
After "thereof" insert -- . --.

Column 12, Line 33:
Delete the second occurrence of "the amount".

Column 12, Line 38:
Delete "further indicate".

Signed and Sealed this
Thirteenth Day of January, 2015

Michelle K. Lee
*Deputy Director of the United States Patent and Trademark Office*